(12) United States Patent
Mustufa et al.

(10) Patent No.: US 10,258,425 B2
(45) Date of Patent: Apr. 16, 2019

(54) MEDICAL ROBOTIC SYSTEM PROVIDING AN AUXILIARY VIEW OF ARTICULATABLE INSTRUMENTS EXTENDING OUT OF A DISTAL END OF AN ENTRY GUIDE

(75) Inventors: Tabish Mustufa, Mountain View, CA (US); Nicola Diolaiti, Palo Alto, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1090 days.

(21) Appl. No.: 12/163,087

(22) Filed: Jun. 27, 2008

(65) Prior Publication Data

US 2009/0326553 A1 Dec. 31, 2009

(51) Int. Cl.

| | |
|---|---|
| *A61B 1/00* | (2006.01) |
| *A61B 90/00* | (2016.01) |
| *A61B 34/30* | (2016.01) |
| *A61B 34/37* | (2016.01) |
| *A61B 34/00* | (2016.01) |
| *A61B 17/00* | (2006.01) |
| *A61B 34/10* | (2016.01) |
| *A61B 34/20* | (2016.01) |

(52) U.S. Cl.
CPC .............. *A61B 90/36* (2016.02); *A61B 34/30* (2016.02); *A61B 34/37* (2016.02); *A61B 34/74* (2016.02); *A61B 34/20* (2016.02); *A61B 90/03* (2016.02); *A61B 90/361* (2016.02); *A61B 2017/00119* (2013.01); *A61B 2034/102* (2016.02); *A61B 2034/305* (2016.02); *A61B 2090/364* (2016.02); *A61B 2090/365* (2016.02)

(58) Field of Classification Search
CPC ... A61B 19/2203; A61B 5/7425; A61B 5/066; G06T 19/00; G06T 2207/10068
USPC ........ 600/424, 426, 104, 102, 173; 606/130; 345/427
See application file for complete search history.

(56) References Cited

U.S. PATENT DOCUMENTS

| | | |
|---|---|---|
| 3,628,535 A | 12/1971 | Ostrowsky et al. |
| 3,818,284 A | 6/1974 | Deversterre et al. |

(Continued)

FOREIGN PATENT DOCUMENTS

| | | |
|---|---|---|
| CN | 101160104 A | 4/2008 |
| EP | 514584 A2 | 11/1992 |

(Continued)

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

(Continued)

*Primary Examiner* — Alexandra L Newton
*Assistant Examiner* — Rynae Boler

(57) ABSTRACT

A medical robotic system includes an entry guide with surgical tools and a camera extending out of its distal end. To supplement the view provided by an image captured by the camera, an auxiliary view including articulatable arms of the surgical tools and/or camera is generated from sensed or otherwise determined information about their positions and orientations and displayed on a display screen from the perspective of a specified viewing point.

2 Claims, 13 Drawing Sheets

(56) References Cited

U.S. PATENT DOCUMENTS

| | | |
|---|---|---|
| 3,905,215 A | 9/1975 | Wright |
| 3,923,166 A | 12/1975 | Fletcher et al. |
| 4,150,326 A | 4/1979 | Engelberger et al. |
| 4,349,837 A | 9/1982 | Hinds |
| 4,577,621 A | 3/1986 | Patel |
| 4,588,348 A | 5/1986 | Beni et al. |
| 4,644,237 A | 2/1987 | Frushour et al. |
| 4,672,963 A | 6/1987 | Barken |
| 4,722,056 A | 1/1988 | Roberts et al. |
| 4,759,074 A * | 7/1988 | Iadipaolo ............... G01N 21/88 382/152 |
| 4,762,455 A | 8/1988 | Coughlan et al. |
| 4,762,456 A | 8/1988 | Nelson |
| 4,791,934 A | 12/1988 | Brunnett |
| 4,815,450 A | 3/1989 | Patel |
| 4,831,549 A | 5/1989 | Red et al. |
| 4,833,383 A | 5/1989 | Skarr et al. |
| 4,837,703 A | 6/1989 | Kakazu et al. |
| 4,837,734 A | 6/1989 | Ichikawa et al. |
| 4,839,838 A | 6/1989 | Labiche et al. |
| 4,853,874 A | 8/1989 | Iwamoto et al. |
| 4,858,149 A | 8/1989 | Quarendon |
| 4,860,215 A | 8/1989 | Seraji |
| 4,863,133 A | 9/1989 | Bonnell |
| 4,891,767 A | 1/1990 | Rzasa et al. |
| 4,942,539 A | 7/1990 | McGee et al. |
| 4,979,949 A | 12/1990 | Matsen, III |
| 4,984,157 A | 1/1991 | Cline et al. |
| 4,989,253 A | 1/1991 | Liang et al. |
| 5,046,022 A | 9/1991 | Conway et al. |
| 5,053,976 A | 10/1991 | Nose et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,174,276 A | 12/1992 | Crockard |
| 5,176,702 A | 1/1993 | Bales et al. |
| 5,182,641 A | 1/1993 | Diner et al. |
| 5,184,009 A | 2/1993 | Wright et al. |
| 5,184,601 A | 2/1993 | Putman |
| 5,187,796 A | 2/1993 | Wang et al. |
| 5,217,003 A | 6/1993 | Wilk |
| 5,230,338 A | 7/1993 | Allen et al. |
| 5,230,623 A | 7/1993 | Guthrie et al. |
| 5,235,510 A | 8/1993 | Yamada et al. |
| 5,239,246 A | 8/1993 | Kim |
| 5,251,127 A | 10/1993 | Raab |
| 5,251,611 A | 10/1993 | Zehel et al. |
| 5,257,203 A | 10/1993 | Riley et al. |
| 5,261,404 A | 11/1993 | Mick et al. |
| 5,266,875 A | 11/1993 | Slotine et al. |
| 5,279,309 A | 1/1994 | Taylor et al. |
| 5,299,288 A | 3/1994 | Glassman et al. |
| 5,313,306 A | 5/1994 | Kuban et al. |
| 5,321,353 A | 6/1994 | Furness |
| 5,337,733 A | 8/1994 | Bauerfeind et al. |
| 5,341,950 A | 8/1994 | Sinz |
| 5,343,385 A | 8/1994 | Joskowicz et al. |
| 5,368,015 A | 11/1994 | Wilk |
| 5,368,428 A | 11/1994 | Hussey et al. |
| 5,382,885 A | 1/1995 | Salcudean et al. |
| 5,397,323 A | 3/1995 | Taylor et al. |
| 5,402,801 A | 4/1995 | Taylor |
| 5,408,409 A | 4/1995 | Glassman et al. |
| 5,417,210 A | 5/1995 | Funda et al. |
| 5,430,643 A | 7/1995 | Seraji |
| 5,445,166 A | 8/1995 | Taylor |
| 5,454,827 A | 10/1995 | Aust et al. |
| 5,474,571 A | 12/1995 | Lang |
| 5,482,029 A | 1/1996 | Sekiguchi et al. |
| 5,493,595 A | 2/1996 | Schoolman |
| 5,503,320 A | 4/1996 | Webster et al. |
| 5,515,478 A | 5/1996 | Wang |
| 5,524,180 A | 6/1996 | Wang et al. |
| 5,528,955 A | 6/1996 | Hannaford et al. |
| 5,531,742 A | 7/1996 | Barken |
| 5,551,432 A | 9/1996 | Iezzi |
| 5,553,198 A | 9/1996 | Wang et al. |
| 5,572,999 A | 11/1996 | Funda et al. |
| 5,601,549 A | 2/1997 | Miyagi |
| 5,617,858 A | 4/1997 | Taverna et al. |
| 5,624,398 A | 4/1997 | Smith et al. |
| 5,631,973 A | 5/1997 | Green |
| 5,638,819 A | 6/1997 | Manwaring et al. |
| 5,657,429 A | 8/1997 | Wang et al. |
| 5,695,500 A | 12/1997 | Taylor et al. |
| 5,704,897 A | 1/1998 | Truppe |
| 5,715,729 A | 2/1998 | Toyama et al. |
| 5,737,500 A | 4/1998 | Seraji et al. |
| 5,748,767 A | 5/1998 | Raab |
| 5,749,362 A | 5/1998 | Funda et al. |
| 5,754,741 A | 5/1998 | Wang et al. |
| 5,755,725 A | 5/1998 | Druais |
| 5,759,151 A | 6/1998 | Sturges |
| 5,759,153 A | 6/1998 | Webler et al. |
| 5,762,458 A | 6/1998 | Wang et al. |
| 5,765,561 A | 6/1998 | Chen et al. |
| 5,784,542 A | 7/1998 | Ohm et al. |
| 5,788,688 A | 8/1998 | Bauer et al. |
| 5,791,231 A | 8/1998 | Cohn et al. |
| 5,792,135 A | 8/1998 | Madhani et al. |
| 5,797,849 A | 8/1998 | Vesely et al. |
| 5,797,900 A | 8/1998 | Madhani et al. |
| 5,807,377 A | 9/1998 | Madhani et al. |
| 5,808,665 A | 9/1998 | Green |
| 5,810,008 A | 9/1998 | Dekel et al. |
| 5,810,880 A | 9/1998 | Jensen et al. |
| 5,814,038 A | 9/1998 | Jensen et al. |
| 5,815,640 A | 9/1998 | Wang et al. |
| 5,817,022 A | 10/1998 | Vesely |
| 5,820,545 A | 10/1998 | Arbter et al. |
| 5,820,623 A | 10/1998 | Ng |
| 5,831,408 A | 11/1998 | Jacobus et al. |
| 5,835,693 A | 11/1998 | Lynch et al. |
| 5,836,880 A | 11/1998 | Pratt |
| 5,841,950 A | 11/1998 | Wang et al. |
| 5,842,473 A | 12/1998 | Fenster |
| 5,842,993 A | 12/1998 | Eichelberger et al. |
| 5,853,367 A | 12/1998 | Chalek et al. |
| 5,855,553 A | 1/1999 | Tajima et al. |
| 5,855,583 A | 1/1999 | Wang et al. |
| 5,859,934 A | 1/1999 | Green |
| 5,876,325 A | 3/1999 | Mizuno et al. |
| 5,877,819 A | 3/1999 | Branson |
| 5,878,193 A | 3/1999 | Wang et al. |
| 5,887,121 A | 3/1999 | Funda et al. |
| 5,907,664 A | 5/1999 | Wang et al. |
| 5,911,036 A | 6/1999 | Wright et al. |
| 5,931,832 A | 8/1999 | Jensen |
| 5,938,678 A | 8/1999 | Zirps et al. |
| 5,950,629 A | 9/1999 | Taylor et al. |
| 5,964,707 A | 10/1999 | Fenster et al. |
| 5,971,976 A | 10/1999 | Wang et al. |
| 5,980,460 A | 11/1999 | Oestensen et al. |
| 5,980,461 A | 11/1999 | Rajan |
| 5,987,591 A | 11/1999 | Jyumonji |
| 5,993,390 A | 11/1999 | Savord et al. |
| 5,993,391 A | 11/1999 | Kamiyama |
| 6,019,724 A | 2/2000 | Gronningsaeter et al. |
| 6,036,637 A | 3/2000 | Kudo |
| 6,059,718 A | 5/2000 | Taniguchi et al. |
| 6,063,095 A | 5/2000 | Wang et al. |
| 6,072,466 A | 6/2000 | Shah et al. |
| 6,083,170 A | 7/2000 | Ben-Haim |
| 6,084,371 A | 7/2000 | Kress et al. |
| 6,096,025 A | 8/2000 | Borders |
| 6,115,053 A | 9/2000 | Perlin |
| 6,120,433 A | 9/2000 | Mizuno et al. |
| 6,129,670 A | 10/2000 | Burdette et al. |
| 6,184,868 B1 | 2/2001 | Shahoian et al. |
| 6,196,081 B1 | 3/2001 | Yau |
| 6,201,984 B1 | 3/2001 | Funda et al. |

(56) References Cited

U.S. PATENT DOCUMENTS

| | | |
|---|---|---|
| 6,204,620 B1 | 3/2001 | McGee et al. |
| 6,224,542 B1 | 5/2001 | Chang et al. |
| 6,226,566 B1 | 5/2001 | Funda et al. |
| 6,241,725 B1 | 6/2001 | Cosman |
| 6,243,624 B1 | 6/2001 | Wu et al. |
| 6,246,200 B1 | 6/2001 | Blumenkranz et al. |
| 6,256,529 B1 | 7/2001 | Holupka et al. |
| 6,270,453 B1 | 8/2001 | Sakai |
| 6,292,712 B1 | 9/2001 | Bullen |
| 6,307,285 B1 | 10/2001 | Delson et al. |
| 6,312,435 B1 | 11/2001 | Wallace et al. |
| 6,325,808 B1 | 12/2001 | Bernard et al. |
| 6,330,837 B1 | 12/2001 | Charles et al. |
| 6,331,181 B1 | 12/2001 | Tierney et al. |
| 6,342,889 B1* | 1/2002 | Callahan ............... 345/427 |
| 6,358,749 B1* | 3/2002 | Orthman ............... G01N 1/04 359/368 |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,402,737 B1 | 6/2002 | Tajima et al. |
| 6,424,885 B1 | 7/2002 | Niemeyer et al. |
| 6,425,865 B1 | 7/2002 | Salcudean et al. |
| 6,434,416 B1 | 8/2002 | Mizoguchi et al. |
| 6,436,107 B1* | 8/2002 | Wang et al. ............... 606/139 |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,522,908 B1 | 2/2003 | Miyashita et al. |
| 6,547,782 B1 | 4/2003 | Taylor |
| 6,550,757 B2 | 4/2003 | Sesek |
| 6,569,084 B1 | 5/2003 | Mizuno et al. |
| 6,574,355 B2 | 6/2003 | Green |
| 6,594,522 B1 | 7/2003 | Korenaga |
| 6,594,552 B1 | 7/2003 | Nowlin et al. |
| 6,599,247 B1 | 7/2003 | Stetten |
| 6,602,185 B1 | 8/2003 | Uchikubo |
| 6,620,173 B2 | 9/2003 | Gerbi et al. |
| 6,642,836 B1 | 11/2003 | Wang et al. |
| 6,643,563 B2 | 11/2003 | Hosek et al. |
| 6,645,196 B1 | 11/2003 | Nixon et al. |
| 6,648,816 B2 | 11/2003 | Irion et al. |
| 6,654,031 B1 | 11/2003 | Ito et al. |
| 6,659,939 B2 | 12/2003 | Moll et al. |
| 6,665,554 B1 | 12/2003 | Charles et al. |
| 6,671,581 B2 | 12/2003 | Niemeyer et al. |
| 6,676,669 B2 | 1/2004 | Charles et al. |
| 6,699,177 B1 | 3/2004 | Wang et al. |
| 6,702,736 B2* | 3/2004 | Chen ............... A61B 1/00009 600/117 |
| 6,714,839 B2 | 3/2004 | Salisbury et al. |
| 6,765,569 B2 | 7/2004 | Neumann et al. |
| 6,770,081 B1 | 8/2004 | Cooper et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,827,712 B2 | 12/2004 | Tovey et al. |
| 6,837,883 B2 | 1/2005 | Moll et al. |
| 6,847,922 B1 | 1/2005 | Wampler, II |
| 6,852,107 B2 | 2/2005 | Wang et al. |
| 6,876,891 B1 | 4/2005 | Schuler et al. |
| 6,905,460 B2 | 6/2005 | Wang et al. |
| 6,926,709 B2 | 8/2005 | Bieger et al. |
| 6,960,162 B2 | 11/2005 | Saadat et al. |
| 6,984,203 B2 | 1/2006 | Tartaglia et al. |
| 6,991,627 B2 | 1/2006 | Madhani et al. |
| 7,041,053 B2 | 5/2006 | Miyake |
| 7,107,090 B2 | 9/2006 | Salisbury et al. |
| 7,107,124 B2 | 9/2006 | Green |
| 7,144,367 B2 | 12/2006 | Chen et al. |
| 7,155,315 B2 | 12/2006 | Niemeyer et al. |
| 7,155,316 B2 | 12/2006 | Sutherland et al. |
| 7,181,315 B2 | 2/2007 | Watanabe et al. |
| 7,194,118 B1 | 3/2007 | Harris et al. |
| 7,302,288 B1 | 11/2007 | Schellenberg |
| 7,413,565 B2 | 8/2008 | Wang et al. |
| 7,491,198 B2 | 2/2009 | Kockro |
| 7,493,153 B2 | 2/2009 | Ahmed et al. |
| 7,574,250 B2 | 8/2009 | Niemeyer |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 7,998,058 B2 | 8/2011 | Kura et al. |
| 8,004,229 B2 | 8/2011 | Nowlin et al. |
| 8,005,571 B2 | 8/2011 | Sutherland et al. |
| 8,062,288 B2 | 11/2011 | Cooper et al. |
| 8,108,072 B2 | 1/2012 | Zhao et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,175,861 B2 | 5/2012 | Huang et al. |
| 8,221,304 B2 | 7/2012 | Shioda et al. |
| 8,256,319 B2 | 9/2012 | Cooper et al. |
| 8,306,656 B1 | 11/2012 | Schaible et al. |
| 8,315,720 B2 | 11/2012 | Mohr et al. |
| 8,335,590 B2 | 12/2012 | Costa et al. |
| 8,398,541 B2 | 3/2013 | Dimaio et al. |
| 8,541,970 B2 | 9/2013 | Nowlin et al. |
| 8,554,368 B2 | 10/2013 | Fielding et al. |
| 8,620,473 B2 | 12/2013 | Diolaiti et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,864,652 B2 | 10/2014 | Diolaiti et al. |
| 8,903,546 B2 | 12/2014 | Diolaiti et al. |
| 8,918,211 B2 | 12/2014 | Diolaiti et al. |
| 8,944,070 B2 | 2/2015 | Guthart et al. |
| 9,084,623 B2 | 7/2015 | Gomez et al. |
| 9,089,256 B2 | 7/2015 | Tognaccini et al. |
| 9,101,397 B2 | 8/2015 | Guthart et al. |
| 9,138,129 B2 | 9/2015 | Diolaiti |
| 9,232,984 B2 | 1/2016 | Guthart et al. |
| 9,333,042 B2 | 5/2016 | Diolaiti et al. |
| 9,345,387 B2 | 5/2016 | Larkin |
| 9,469,034 B2 | 10/2016 | Diolaiti et al. |
| 9,492,927 B2 | 11/2016 | Diolaiti et al. |
| 9,516,996 B2 | 12/2016 | Diolaiti et al. |
| 9,565,990 B2 | 2/2017 | Lee et al. |
| 9,622,826 B2 | 4/2017 | Diolaiti et al. |
| 9,629,520 B2 | 4/2017 | Diolaiti |
| 9,717,563 B2 | 8/2017 | Tognaccini et al. |
| 9,718,190 B2 | 8/2017 | Larkin et al. |
| 9,949,798 B2 | 4/2018 | Weir et al. |
| 2001/0035871 A1 | 11/2001 | Bieger et al. |
| 2002/0044104 A1 | 4/2002 | Friedrich et al. |
| 2002/0045888 A1 | 4/2002 | Ramans et al. |
| 2002/0045905 A1 | 4/2002 | Gerbi et al. |
| 2002/0089544 A1 | 7/2002 | Jahn et al. |
| 2002/0120188 A1 | 8/2002 | Brock et al. |
| 2002/0156345 A1 | 10/2002 | Eppler et al. |
| 2002/0193800 A1 | 12/2002 | Kienzle, III |
| 2003/0023347 A1 | 1/2003 | Konno et al. |
| 2003/0032878 A1 | 2/2003 | Shahidi |
| 2003/0055410 A1* | 3/2003 | Evans et al. ............... 606/1 |
| 2003/0060927 A1 | 3/2003 | Gerbi et al. |
| 2003/0109780 A1 | 6/2003 | Coste-Maniere et al. |
| 2003/0114730 A1 | 6/2003 | Hale et al. |
| 2003/0144649 A1 | 7/2003 | Ghodoussi et al. |
| 2003/0167103 A1 | 9/2003 | Tang et al. |
| 2003/0220541 A1 | 11/2003 | Salisbury, Jr. et al. |
| 2003/0225479 A1 | 12/2003 | Waled |
| 2004/0024311 A1 | 2/2004 | Quaid et al. |
| 2004/0034283 A1 | 2/2004 | Quaid, III |

(56) References Cited

U.S. PATENT DOCUMENTS

| | | |
|---|---|---|
| 2004/0039485 A1 | 2/2004 | Niemeyer et al. |
| 2004/0044295 A1 | 3/2004 | Reinert et al. |
| 2004/0046711 A1 | 3/2004 | Triebfuerst |
| 2004/0046916 A1 | 3/2004 | Lyu et al. |
| 2004/0049205 A1 | 3/2004 | Lee et al. |
| 2004/0077940 A1 | 4/2004 | Kienzle et al. |
| 2004/0106916 A1 | 6/2004 | Quaid et al. |
| 2004/0176751 A1 | 9/2004 | Weitzner et al. |
| 2004/0189675 A1 | 9/2004 | Pretlove et al. |
| 2004/0225183 A1 | 11/2004 | Michlitsch et al. |
| 2004/0238732 A1* | 12/2004 | State et al. ............ 250/250 |
| 2004/0243147 A1 | 12/2004 | Lipow |
| 2004/0249508 A1 | 12/2004 | Suita et al. |
| 2004/0254454 A1 | 12/2004 | Kockro |
| 2004/0254679 A1 | 12/2004 | Nagasaka |
| 2005/0022158 A1* | 1/2005 | Launay et al. ............ 717/104 |
| 2005/0054895 A1* | 3/2005 | Hoeg et al. ............ 600/117 |
| 2005/0059960 A1 | 3/2005 | Simaan et al. |
| 2005/0096502 A1* | 5/2005 | Khalili ............ 600/106 |
| 2005/0096892 A1 | 5/2005 | Watanabe et al. |
| 2005/0107680 A1 | 5/2005 | Kopf et al. |
| 2005/0113640 A1 | 5/2005 | Saadat et al. |
| 2005/0166413 A1 | 8/2005 | Crampton et al. |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2005/0267359 A1 | 12/2005 | Hussaini et al. |
| 2006/0058988 A1 | 3/2006 | Defranoux et al. |
| 2006/0142657 A1 | 6/2006 | Quaid et al. |
| 2006/0149129 A1 | 7/2006 | Watts et al. |
| 2006/0161045 A1 | 7/2006 | Merril et al. |
| 2006/0161138 A1 | 7/2006 | Orban, III |
| 2006/0178559 A1 | 8/2006 | Kumar et al. |
| 2006/0241414 A1 | 10/2006 | Nowlin et al. |
| 2006/0258938 A1* | 11/2006 | Hoffman et al. ............ 600/424 |
| 2006/0261770 A1 | 11/2006 | Kishi et al. |
| 2007/0013336 A1 | 1/2007 | Nowlin et al. |
| 2007/0016174 A1 | 1/2007 | Millman et al. |
| 2007/0021738 A1 | 1/2007 | Hasser et al. |
| 2007/0032906 A1 | 2/2007 | Sutherland et al. |
| 2007/0038080 A1* | 2/2007 | Salisbury et al. ............ 600/427 |
| 2007/0060879 A1 | 3/2007 | Weitzner et al. |
| 2007/0071310 A1 | 3/2007 | Kobayashi et al. |
| 2007/0081714 A1 | 4/2007 | Wallack et al. |
| 2007/0106307 A1 | 5/2007 | Bodduluri et al. |
| 2007/0135803 A1 | 6/2007 | Belson |
| 2007/0138992 A1 | 6/2007 | Prisco et al. |
| 2007/0142825 A1* | 6/2007 | Prisco ............ B25J 9/1674 606/1 |
| 2007/0142968 A1 | 6/2007 | Prisco et al. |
| 2007/0144298 A1 | 6/2007 | Miller |
| 2007/0156285 A1 | 7/2007 | Sillman et al. |
| 2007/0177009 A1 | 8/2007 | Bayer et al. |
| 2007/0197896 A1 | 8/2007 | Moll et al. |
| 2007/0229015 A1 | 10/2007 | Yoshida et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0270685 A1 | 11/2007 | Kang et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2007/0296366 A1 | 12/2007 | Quaid et al. |
| 2008/0004603 A1 | 1/2008 | Larkin et al. |
| 2008/0033240 A1 | 2/2008 | Hoffman et al. |
| 2008/0065099 A1 | 3/2008 | Cooper et al. |
| 2008/0065105 A1 | 3/2008 | Larkin et al. |
| 2008/0065109 A1 | 3/2008 | Larkin |
| 2008/0071291 A1 | 3/2008 | Duval et al. |
| 2008/0081992 A1 | 4/2008 | Kagermeier |
| 2008/0118115 A1 | 5/2008 | Williamson |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0005640 A1 | 1/2009 | Fehre et al. |
| 2009/0012531 A1 | 1/2009 | Quaid et al. |
| 2009/0024142 A1 | 1/2009 | Ruiz |
| 2009/0036902 A1 | 2/2009 | Dimaio et al. |
| 2009/0088634 A1 | 4/2009 | Zhao et al. |
| 2009/0105750 A1 | 4/2009 | Price et al. |
| 2009/0192523 A1 | 7/2009 | Larkin et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 | 10/2009 | Miyano et al. |
| 2009/0326318 A1 | 12/2009 | Tognaccini et al. |
| 2009/0326322 A1 | 12/2009 | Diolaiti |
| 2009/0326552 A1 | 12/2009 | Diolaiti |
| 2009/0326556 A1 | 12/2009 | Diolaiti et al. |
| 2009/0326711 A1 | 12/2009 | Chang et al. |
| 2010/0004505 A1 | 1/2010 | Umemoto et al. |
| 2010/0036198 A1 | 2/2010 | Tacchino et al. |
| 2010/0106356 A1 | 4/2010 | Trepagnier et al. |
| 2010/0169815 A1 | 7/2010 | Zhao et al. |
| 2010/0198232 A1 | 8/2010 | Diolaiti |
| 2010/0228264 A1 | 9/2010 | Robinson et al. |
| 2010/0249657 A1 | 9/2010 | Nycz et al. |
| 2010/0274087 A1 | 10/2010 | Diolaiti et al. |
| 2010/0317965 A1 | 12/2010 | Itkowitz et al. |
| 2010/0331855 A1 | 12/2010 | Zhao et al. |
| 2010/0331856 A1 | 12/2010 | Carlson et al. |
| 2011/0040305 A1 | 2/2011 | Gomez et al. |
| 2011/0040404 A1 | 2/2011 | Diolaiti et al. |
| 2011/0071675 A1 | 3/2011 | Wells et al. |
| 2011/0105898 A1 | 5/2011 | Guthart et al. |
| 2011/0196199 A1 | 8/2011 | Donhowe et al. |
| 2011/0202068 A1 | 8/2011 | Diolaiti et al. |
| 2011/0290856 A1 | 12/2011 | Shelton, IV et al. |
| 2011/0313573 A1 | 12/2011 | Schreiber et al. |
| 2012/0059391 A1 | 3/2012 | Diolaiti et al. |
| 2012/0059392 A1 | 3/2012 | Diolaiti |
| 2012/0132450 A1 | 5/2012 | Timm et al. |
| 2012/0154564 A1 | 6/2012 | Hoffman et al. |
| 2013/0178868 A1 | 7/2013 | Roh |
| 2013/0231680 A1 | 9/2013 | Diolaiti et al. |
| 2013/0245375 A1 | 9/2013 | Dimaio et al. |
| 2013/0289767 A1 | 10/2013 | Lim et al. |
| 2014/0051922 A1 | 2/2014 | Guthart et al. |
| 2014/0052150 A1 | 2/2014 | Taylor et al. |
| 2014/0055489 A1 | 2/2014 | Itkowitz et al. |
| 2014/0135792 A1 | 5/2014 | Larkin et al. |
| 2014/0222021 A1 | 8/2014 | Diolaiti et al. |
| 2014/0232824 A1 | 8/2014 | Dimaio et al. |
| 2015/0032126 A1 | 1/2015 | Nowlin et al. |
| 2015/0051733 A1 | 2/2015 | Nowlin et al. |
| 2015/0065793 A1 | 3/2015 | Diolaiti et al. |
| 2015/0150639 A1 | 6/2015 | Diolaiti et al. |
| 2015/0182287 A1 | 7/2015 | Guthart et al. |
| 2015/0297300 A1 | 10/2015 | Gomez et al. |
| 2015/0366625 A1 | 12/2015 | Tognaccini et al. |
| 2016/0045272 A1 | 2/2016 | Diolaiti |
| 2016/0235486 A1 | 8/2016 | Larkin |
| 2016/0242860 A1 | 8/2016 | Diolaiti et al. |
| 2016/0374767 A1 | 12/2016 | Diolaiti et al. |
| 2017/0035521 A1 | 2/2017 | Diolaiti et al. |
| 2017/0173788 A1 | 6/2017 | Diolaiti et al. |
| 2017/0209232 A1 | 7/2017 | Larkin et al. |
| 2017/0210012 A1 | 7/2017 | Larkin et al. |

FOREIGN PATENT DOCUMENTS

| | | |
|---|---|---|
| EP | 0646358 A1 | 4/1995 |
| EP | 812662 A1 | 12/1997 |
| EP | 812662 A1 | 12/1997 |
| EP | 1125557 A2 | 8/2001 |
| EP | 0732082 B1 | 9/2002 |
| EP | 1310844 A1 | 5/2003 |
| EP | 1424173 A2 | 6/2004 |
| JP | S61230895 A | 10/1986 |
| JP | H01280449 A | 11/1989 |
| JP | H04231034 A | 8/1992 |

(56) References Cited

FOREIGN PATENT DOCUMENTS

| | | |
|---|---|---|
| JP | H07184923 A | 7/1995 |
| JP | H07265321 A | 10/1995 |
| JP | H0889506 A | 4/1996 |
| JP | H08107875 A | 4/1996 |
| JP | H08132372 A | 5/1996 |
| JP | H08154321 A | 6/1996 |
| JP | H08215211 A | 8/1996 |
| JP | H08275958 A | 10/1996 |
| JP | H08299363 A | 11/1996 |
| JP | H09141580 A | 6/1997 |
| JP | H10146341 A | 6/1998 |
| JP | H11000309 A | 6/1999 |
| JP | 2000500679 A | 1/2000 |
| JP | 2000300579 A | 10/2000 |
| JP | 2001000448 A | 1/2001 |
| JP | 2001061850 A | 3/2001 |
| JP | 2001104333 A | 4/2001 |
| JP | 2001202531 A | 7/2001 |
| JP | 2001287183 A | 10/2001 |
| JP | 2002103258 A | 4/2002 |
| JP | 2002287613 A | 10/2002 |
| JP | 2003053684 A | 2/2003 |
| JP | 2003300444 A | 10/2003 |
| JP | 2003339725 A | 12/2003 |
| JP | 2004105638 A | 4/2004 |
| JP | 2004223128 A | 8/2004 |
| JP | 2005110878 A | 4/2005 |
| JP | 2005135278 A | 5/2005 |
| JP | 2005303327 A | 10/2005 |
| JP | 2005334650 A | 12/2005 |
| JP | 2007029232 A | 2/2007 |
| JP | 2007090481 A | 4/2007 |
| JP | 2007508913 A | 4/2007 |
| JP | 2007531553 A | 11/2007 |
| JP | 2009006410 A | 1/2009 |
| JP | 2009012106 A | 1/2009 |
| JP | 2009039814 A | 2/2009 |
| JP | 2009525097 A | 7/2009 |
| JP | 2009537229 A | 10/2009 |
| KR | 20090111308 A | 10/2009 |
| WO | WO-199501757 | 1/1995 |
| WO | WO-9507055 A1 | 3/1995 |
| WO | WO-9729690 A1 | 8/1997 |
| WO | WO-9743942 A1 | 11/1997 |
| WO | WO-9743943 A1 | 11/1997 |
| WO | WO-03061482 A1 | 7/2003 |
| WO | WO2004014244 A2 | 2/2004 |
| WO | WO-2005037120 A1 | 4/2005 |
| WO | WO-2005039391 A2 | 5/2005 |
| WO | WO-2005043319 A2 | 5/2005 |
| WO | WO-2006079108 A1 | 7/2006 |
| WO | WO-2006091494 A1 | 8/2006 |
| WO | WO-2007005555 A2 | 1/2007 |
| WO | WO-2007030173 A1 | 3/2007 |
| WO | WO-200747782 A2 | 4/2007 |
| WO | 2007088208 A1 | 8/2007 |
| WO | WO-2007088206 A2 | 8/2007 |
| WO | WO-2007088208 A1 | 8/2007 |
| WO | WO-2007136768 A2 | 11/2007 |
| WO | WO-07146987 A2 | 12/2007 |
| WO | WO-08002830 A1 | 1/2008 |
| WO | WO-2008094766 A2 | 8/2008 |
| WO | WO-2008103383 A1 | 8/2008 |
| WO | WO2009034477 A2 | 3/2009 |
| WO | WO2009037576 A2 | 3/2009 |
| WO | WO-2009044287 A2 | 4/2009 |
| WO | 2009158164 A1 | 12/2009 |
| WO | WO-2009158164 A1 | 12/2009 |
| WO | 201039394 | 4/2010 |
| WO | WO-2010039394 A1 | 4/2010 |

OTHER PUBLICATIONS

PCT/US07/71850 International Search Report and Written Opinion of the International Searching Authority, dated Feb. 13, 2009, 9 pages.

PCT/US09/46234 International Search Report and Written Opinion of the International Searching Authority, dated Sep. 9, 2009, 13 pages.

PCT/US10/28897 International Search Report and Written Opinion of the International Searching Authority, dated Jul. 19, 2010, 16 pages.

PCT/US10/38246 International Search Report and Written Opinion of the International Searching Authority, dated Sep. 14, 2010, 17 pages.

3D Slicer web site,http//www.slicer.org,2003.

Abolmaesumi, Purang et al., "A User Interface for Robot-Assisted Diagnostic Ultrasound," IEEE Robotics and Automation Conference, 2001, pp. 1549-1554, vol. 2, IEEE.

Abolmaesumi, Purang et al., "Image Guided Control of a Robot for Medical Ultrasound," IEEE Transactions on Robotics and Automation, 2002, pp. 11-23, vol. 18—Issue 1, IEEE.

Adams, Ludwig et al., "Computer-Assisted Surgery," IEEE Computer Graphics & Applications, May 1990, pp. 43-52, vol. 10—Issue 3, IEEE Computer Society Press.

Ahlering, Thomas. E. et al., "Robotic radical prostatectomy: a technique to reduce pT2 positive margins," Urology, 2004, pp. 1224-1228, vol. 64 Issue 6, Elsevier Inc.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26 1984, pp. 40-45, vol. 1.

Arun, K.S. et al., "Least-Squares Fitting of Two 3-D Point Sets," IEEE Transactions on Pattern Analysis and Machine Intelligence (PAMI), vol. 9, No. 5, pp. 698-700, Sep. 1987.

Askew, Scott R. et al., "Ground control testbed for space station freedom robot manipulators," IEEE Virtual Reality Annual International Symposium, 1993, pp. 69-75, IEEE.

Azuma, Ronald T., "A Survey of Augmented Reality," Teleoperators and Virtual Environments, 1997, pp. 355-385, vol. 6—No. 4.

Bajura, Michael et al., "Merging Virtual Objects with the Real World: Seeing Ultrasound Imagery within the Patient," Computer Graphics, Jul. 26, 1992, pp. 203-210, vol. 26, Issue 2, ACM Press.

Banovac, Filip et al., "Liver Tumor Biopsy in a Respiring Phantom with the Assistance of a Novel Electromagnetic Navigation Device," 2002, pp. 200-207, Springer-Verlag.

Bartels, Richard H. et al., "An Introduction to Splines for use in Computer Graphics and Geometric Modeling," 1987, 6 Pages total , Morgan kaufmann publishers, Inc.

Bartels, Richard H. et al., "Solution of the Matrix Equation AX+XB=C," Communications of the ACM, 1972, pp. 820-826, vol. 15—Issue 9, ACM Press.

Baumann, Roger, "Haptic Interface for Virtual Reality Based Laparoscopic Surgery Training Environment," These No. 1734 Ecole Pholytechnique Federale de Lausanne, 1997, 104 Total Pages.

Bejczy, Antal K. et al., "Controlling Remote Manipulators through Kinesthetic Coupling," Computers in Mechanical Engineering, 1983, pp. 48-60, vol. 1—Issue 1.

Ben Gayed, M. et al., "An Advanced Control Micromanipulator for Surgical Applications," Systems Science, 1987, pp. 123-134, vol. 13.

Berkelman, Peter J. et al., "A Compact Compliant Laparoscopic Endoscope Manipulator," IEEE International Conference on Robotics and Automation, 2002, pp. 1870-1875, vol. 2, IEEE.

Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.

Berkelman, Peter J. et al., "A miniature microsurgical instrument tip force sensor for enhanced force feedback during robot-assisted manipulation," IEEE Transactions on Robotics and Automation, 2000, pp. 917-921, vol. 19—Issue 5, IEEE.

(56) References Cited

OTHER PUBLICATIONS

Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.
Besl, Paul J. et al., "A Method for Registration of 3-D Shapes," IEEE Transactions on Pattern Analysis and Machine Intelligence (PAMI), vol. 14, Issue 2, pp. 239-256, Feb. 1992.
Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.
Bettini, Alessandro et al., "Vision Assisted Control for Manipulation Using Virtual Fixtures," IEEE Transactions on Robotics, 2004, pp. 953-966, vol. 20—Issue 6, IEEE.
Birkett, Desmond H., "Three-Dimensional Video Imaging Systems," Chapter 1 in Primer of Robotic & Telerobotic Surgery, Eds. Garth H. Ballantyne et al., Pub. by Lippincott Williams & Wilkins, Philadelphia, 2004, pp. 7-11.
Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.
Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.
Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.
Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, pp. 46, vol. 6—Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science, 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Borovoi, A.V., "Stability of a manipulator with force feedback," Izv. AN SSSR Mekhanika Tverdogo Teal, 1990, pp. 37-45, vol. 25—Issue 1, Allerton Press, Inc.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burdea, Grigore et al., "Dextrous Telerobotics with Force Feedback—an overview. Part 2: Control and Implementation," Robotica, 1991, pp. 291-298, vol. 9.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Bzostek, Andrew, "Computer-Integrated needle therapy systems: Implementation and Analysis," Computer Science, 2005, 379 pages.
Bzostek, Andrew et al., "A Testbed System for Robotically Assisted Percutaneous Pattern Therapy," Medical Image Computing and Computer-Assisted Surgery, Lecture Notes in Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes in Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. 2007-01-2007-22.
Cadeddu, Jeffrey A. et al., "A Robotic System for Percutaneous Renal Access," The Journal of Urology, 1997, pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Cao, Caroline L., et al., "Task and motion analysis in endoscopic surgery," Submitted for Fifth Annual Symposium on Haptic Interfaces for Virtual Environment and Teloperator Systems for the Winter Meeting of ASME, 1996, pp. 1-32.
Carr, J., "Surface reconstruction in 3D medical imaging," PhD Thesis, University of Canterbury, Christchurch, New Zealand, 1996, 223 Pages.
Cash, David M. et al., "Incorporation of a laser range scanner into an image-guided surgical system," The International Society for Optical Engineering (SPIE), Medical Imaging 2003: Visualization, Image-Guided Procedures, and Display; San Diego, CA, Ed. Robert L. Galloway, 2003, pp. 269-280, vol. 5029.
Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.
Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.

(56) References Cited

OTHER PUBLICATIONS

Christensen, B. et al., "Model based sensor directed remediation of underground storage tanks," International Conf. on Robotics and Automation, Sacramento, CA, Apr. 1991, pp. 1377-1383, vol. 2. IEEE.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
Cohn, Michael C., "Medical Robotics," http://www-bsac.eecs.berkeley.edu/ , 1996, pp. 1-8 and 4.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 2000, pp. 286-298, vol. 19—No. 3, Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S. C.et al., "Ultrasound quantitaion of respiratory organ motion in the upper abdomen," British Journal of Radiology, 1994, pp. 1096-1102, vol. 37—Iss. 803.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Debus, Thomas et al., "Multichannel Vibrotactile Display for Sensory Substitution During Teleoperation," Proc. SPIE Telemanipulator and Telepresence Technologies VIII, 2001, pp. 42-49, vol. 4570, SPIE.
Degoulange, E. et al., "Hippocrate: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 2, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, pp. 4.
Dolan, J.M. et al., "A Robot in an Operating Room: A Bull in a China Shop," 1987, pp. 1096-1097, vol. 2.
Elder, Matthew C. et al., "Specifying user interfaces for safety critical medical systems," Second Annual International Symposium on Medical Robotics and Computer Assisted Surgery, Nov. 1995, pp. 148-155.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System for Robotically Assisted Prostate Biopsy and Therapy With intraOperative CT Guidance," Journal of Academic Radiology, 2002, pp. 60-74, vol. 9 No. 1, Elsevier.
Fisher, Scott S., "Virtual interface environment," IEEE/A1AA 7th Digital Avionics Systems Conference Ft. Worth Texas, 1986, pp. 346-350, IEEE.
Frantz D.D et al., "Accuracy assessment protocols for electromagnetic tracking systems," Physics in Medicine and Biology, 2003, pp. 2241-2251, Issue 48.
Fu, K.S. et al., "Robotics: control, sensing, vision, and intelligence," 1987, pp. 12-76 and 201-265, Ch. 2 & 5, McGraw-Hill Book Company.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Fukuda, Toshio et al., "A new method of master-slave type of teleoperation for a micro-manipulator system," IEEE Microrobots and Teleoperations Workshop, 1987, 5 pages, IEEE.
Funda, Janez, "An experimental user interface for an interactive surgical robot," In 1st International Symposium on Medical Robotics and Computer Assisted Surgery (MRCAS 94), Pittsburgh, 1994, pp. 196-201, 203.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Furuta, Katsuhisa et al., "Master slave manipulator based on virtual internal model following control concept," IEEE Intl. Conference on Robotics and Automation, 1987, pp. 567-572, vol. 1, IEEE.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, Arthur et al., "Applied Optimal Estimation," 1974, 4 Pages Total.

(56) References Cited

OTHER PUBLICATIONS

Gennari, G. et al., "Probabilistic data association methods in visual tracking of groups," IEEE Conference on Computer Vision and Pattern Recognition, 2004, pp. I-790-1-797, vol. 1—issue. 27, IEEE.
Gigot, Jean-Francois et al., "Laparoscopic Liver Resection for Malignant Liver Tumors Prelimary Results of a Multicenter European Study," Ann Surg, 2002, pp. 90-97, vol. 236—issue 1.
Gonzales, Adriana Vilchis et al., "A System for Robotic Tele-echography," Medical Image Computing and Computer-Assisted Intervention, 2001, pp. 326-334, vol. 2208, Springer.
Green, Philip, S. et al., "Mobile telepresence surgery," 2nd Annual Intl Symposium on Med. Robotics and Computer Assisted Surgery, Maryland Nov. 1995, pp. 97-103.
Grimson, W. Eric et al., "Automated Registration for Enhanced Reality Visualization in Surgery," 1st International Symposium on Medical Robotic and Computer Assisted Surgery (MRCAS), Pittsburgh, 1994, pp. 82-89.
Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.
Hager, Gregory D., "A Modular System for Robust Hand Eye Coordination Using Feedback from Stereo Vision," IEEE Transactions on Robotics and Automation, 1997, pp. 582-595, vol. 13—issue(4), IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.
Hager, Gregory D. et al., "The XVision System: A Portable Substrate for Real Time Vision Applications," 1998, pp. 23-37, vol. 69—issue 1.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "A robotic procedure for transurethral resection of the prostate," Second Annual International Symposium on Medical Robotics and Computer Assisted Surgery, 1995, pp. 264-271.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline, Alan J. et al., "Image-Guided Surgery: Preliminary Feasibility Studies of Frameless Stereotactic Liver Surgery," Archives of Surgery, 1999, pp. 644-650, vol. 134—No. 6.
Herline, Alan J. et al., "Surface Registration for Use in Interactive," Image-Guided Liver Surgery, Computer Aided Surgery, 2000, pp. 11-17, vol. 5—No. 2.
Herman, Barry C., et al, "Telerobotic surgery creates opportunity for augmented reality surgery," Abstract No. T1F2, Telemedicine Journal and E-Health, vol. 11, Issue 2, p. 203, Apr. 2005.
Herman, Barry C., "On the Role of Three Dimensional Visualization for Surgical Applications in Interactive Human Machine Systems," Masters of Science Thesis in Computer Science, The Johns Hopkins University, Baltimore, 2005, 216 pages.
Hespanha J.P. et al., "What Tasks Can Be Performed with an Uncalibrated Stereo Vision System", International Journal of Computer Vision, 1999, pp. 65-85, vol. 35—issue. (1).
Hill, John W., "Telepresence surgery demonstration system," Robotics and Automation, 1994, pp. 2302-2307, vol. 3, SRI International.
Ho, S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Horn, Berthold K.P., "Closed-form solution of absolute orientation using unit quaternions," Journal of the Optical Society of America A, vol. 4, No. 4, pp. 629-642, Apr. 1987.
Hunter, Ian W. et al., "A teleoperated microsurgical robot and associated virtual environment for eye surgery," Presence: Teleoperators and Virtual Environments, 1993, pp. 265-280, vol. 2—No. 4, MIT Press.
Hunter, Ian W. et al., "Ophthalmic microsurgical robot and associated virtual environment," Comput. Biol. Med, 1995, vol. 25, Issue 2, pp. 173-182, Pergamon.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Hutchinson, Seth et al., "A Tutorial Visual Servo Control," IEEE Transactions on Robotics and Automation, 1996, pp. 651-670, vol. 12 issue.5, IEEE.
IEEE Systems and Software Engineering—Recommended Practice for Architectural Description of Software-Intensive Systems, IEEE Std 1471-2000, 34 pages, First Edition, Jul. 15, 2007.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
Intuitive Surgical, Inc., "Intuitive Surgical daVinci API v5.0 Reference Manual," generated Jul. 17, 2006, 149 pages.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Johns Hopkins University and Intuitive Surgical, Inc., "System Requirements for the Surgical Assistant Workstation," Rev. 2, Jan. 29, 2007, 17 pages.
Jones, Daniel B. et al., "Next generation 3D videosystems may improve laprascopic task performance," Interactive Technology and the New Paradigm for Healthcare, 1995, pp. 152-160, Ch 25.
Joskowicz, Leo et al., "Computers in Imaging and Guided Surgery," Computing in Science and Engineering, 2001, pp. 65-72, vol. 3—Issue: 5, IEEE.
Jurie, Frederic et al., "Hyperplane Approximation for Template Matching," IEEE Transactions on Pattern Analysis and Machine lntelligence(PAMI), 2002, pp. 996-1000, vol. 24—Issue 7, IEEE.
Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor, Ankur and Russell H. Taylor, "A constrained optimization approach to virtual fixtures for multi-handed tasks," 2008 International Conference on Robotics and Automation (ICRA 2008), May 19-23, 2008, Pasadena, California, pp. 3401-3406.
Kapoor, Ankur et al., "Constrained Control for Surgical Assistant Robots," 2006 IEEE International Conference on Robotics and Automation (ICRA 2006), Orlando, Florida, May 15-19, 2006, pp. 231-236.
Kapoor, Ankur et al., "Simple Biomanipulation Tasks with a Steady Hand Cooperative Manipulator," In Proceedings of the Sixth International Conference on Medical Image Computing and Computer Assisted Intervention—MICCAI,, Lecture Notes in Computer Science, 2003, vol. 1, Springer.

(56) References Cited

OTHER PUBLICATIONS

Kapoor, Ankur et al., "Suturing in Confined Spaces: Constrained Motion Control of a Hybrid 8-DOF Robot," Proceedings, 12th International Conference on Advanced Robotics, 2005, pp. 452-459.
Kavoussi, Louis R., "Laparoscopic donor nephrectomy," Kidney International, 2000, pp. 2175-2186, vol. 57.
Kazanzides, Peter et al., "A cooperatively-controlled image guided robot system for skull base surgery," Medicine Meets Virtual Reality 16 (MMVR 16) Conference, Jan. 30-Feb. 1, 2008, Long Beach, California, J.D. Westwood et al., eds., IOS Press, 2008, pp. 198-203.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H. , "Human Extenders," ASME J. Dynamic Systems, Measurements and Control, 1993, pp. 281-290, vol. 115 No. 2(B).
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kilmer, R. D. et al., "Watchdog safety computer design and implementation," RI/SME Robots 8 Conference, Jun. 1984, pp. 101-117.
Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.
Kitagawa, Masaya et al., "Effect of Sensory Substitution on Suture Manipulation Forces for Surgical Teleoperation," 12th Annual Medicine Meets Virtual Reality Conference, 2005, 8 pages.
Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Komada, Satoshi et al., "Bilateral robot hand based on estimated force feedback," IEEE Proceedings IECON 87 Cambridge MA, Nov. 3-6, 1987, pp. 602-607, vol. 2, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kosugi, Yukio et al., "An articulated neurosurgical navigation system using MRI and CT Images," IEEE Transactions on Biomedical Engineering, 1988, pp. 147-152, vol. 35—Issue 2, IEEE.
Kragic D. et al., "Human-Machine Collaborative Systems for Microsurgical Applications," International Symposium on Robotics Research, 2005, pp. 731-741, vol. 24—Issue 9, Sage Publications.
Kruchten, Philippe B., "The 4+1 View Model of Architecture," IEEE Software, vol. 12, Issue 6, pp. 42-50, Nov. 1995.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention—Part , Lecture Notes in Computer Science, 2002, pp. 9-16, vol. 2488, Springer Verlag.
Kumar, Rajesh, "An Augmented Steady Hand System for Precise Micromanipulation," 2001, 109 pages.
Kumar, Rajesh et al., "An Augmentation System for Fine Manipulation," Proceedings of the Third International Conference on Medical Image Computing and Computer-Assisted Intervention, Lecture Notes in Computer Science, 2000, pp. 956-964, vol. 1935, Springer Verlang.
Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes in Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Lacroute, Philippe et al., "The VolPack Volume Rendering Library," 2003, pp. 4.
Lacroute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.
Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.
Lawson, Charles L. et al., "Linear least squares with linear inequality constraints Solving Least Squares Problems," 1974, pp. 158-173, Prentice Hall Inc.
Lazarevic, Zoran, "Feasibility of a Stewart Platform with Fixed Actuators as a Platform for CABG Surgery Device," 1997, 45 pages, Master's Thesis Columbia University Department of Bioengineering.
Lee Jr, Fred T. et al., "CT-monitored percutaneous cryoablation in a pig liver model," Radiology, 1999, pp. 687-692, vol. 211(3).
Leven, Joshua, "A Telerobotic Surgical System With Integrated Robot-Assisted Laparoscopic Ultrasound Capability," Thesis for Master of Science in Engineering in Computer Science, The Johns Hopkins University, Baltimore, Maryland, May 2005, 63 pages.
Leven, Joshua et al. "DaVinci Canvas: A Telerobotic Surgical System with Integrated, Robot-Assisted, Laparoscopic Ultrasound Capability," Medical Image Computing and Computer-Assisted Intervention (MICCAI), Lecture Notes in Computer Science, J. Duncan et al. Eds., Palm Spring, Springer Verlag, 2005, vol. 3749, pp. 811-818.
Levoy, Marc, "Display of Surfaces from Volume Data," IEEE Computer Graphics and Applications, 1988, pp. 29-37, vol. 8—Iss. 3, IEEE.
Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.

(56) References Cited

OTHER PUBLICATIONS

Li, Ming and Russell H. Taylor, "Performance of surgical robots with automatically generated spatial virtual fixtures," IEEE International Conference on Robotics and Automation, Barcelona, Spain, Apr. 2005, pp. 217-222.

Li, Ming et al, "A Constrained Optimization Approach to Virtual Fixtures," IEEE/RSJ International Conference on Intelligent Robots and Systems (IROS 2005), Edmonton, Alberta, Canada, Aug. 2-6, 2005, pp. 1408-1413.

Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.

Li, Ming et al., "Recognition of Operator Motions for Real-Time Assistance using Virtual Fixtures," IEEE, Haptics 2003, 11th Symposium on Haptic Interfaces for Virtual Environment and Teleoperator Systems, Mar. 22-23, 2003, pp. 125-131, IEEE.

Li, Ming, "Intelligent Robotic Surgical Assistance for Sinus Surgery," Ph.D. Dissertation, Computer Science, Johns Hopkins University, Baltimore, 2005, 229 pages.

Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.

Loser, Michael H. et al., "Visual servoing for automatic and uncalibrated percutaneous procedures," SPIE Medical Imaging, 2000, pp. 270-281, vol. 3976, SPIE.

Madhani, Akhil J., "Design of Teleoperated Surgical Instruments for Minimally Invasive Surgery," Feb. 1998, pp. 1-251.

Maehara, S. et al., "Laparoscopy-Assisted Hepatectomy Using the Endoclose," Surg Endosc, 2002, pp. 1362-1365, vol. 16(9), Springer Verlag.

Maier, Georg, E. et al., "A Dynamically Configurable General Purpose Automation Controller," Proceedings of IFAC/IFIP Symp. on Software for Computer Control, 1986, pp. 47-52, Pergamon Press.

Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.

Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.

Marescaux, Jadques and Francesco Rubino, "Virtual Operative Fields for Surgical Simulation," Chapter 4 in Primer of Robotic & Telerobotic Surgery, Eds. Garth H. Ballantyne et al., Pub. by Lippincott Williams & Wilkins, Philadelphia, 2004, pp. 26-31.

Masamune K., et al., "Development of a MRI Compatible Needle Insertion Manipulator for Stereotactic Neurosurgery," Journal of Image Guided Surgery, 1995, vol. 1, pp. 242-248.

Masamune, Ken et al., "Development of a MRI Compatible Needle Insertion Manipulator for Stereotactic Neurosurgery," Image Guid Surg, 1995, pp. 165-172.

Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.

Masamune, Ken et al., "System for Robotically Assisted Percutaneous Procedures With Computed Tomography Guidance," Journal of Computer-Assisted Surgery, 2001, pp. 370-383, vol. 6—No. 6, Wiley-Liss, Inc.

Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.

Massie, Thomas H. et al., "The Phantom Haptic Interface: A Device for Probing Virtual Objects," Proceedings of the ASME Winter Annual Meeting, Symposium on Haptic Interfaces for Virtual Environment and Teleoperator Systems, 1994, 7 pages.

Mayer, Hermann et al., "Skill Transfer and Learning by Demonstration in a Realistic Scenario of Laparoscopic Surgery," International Conference on Humanoids, 2003, 17 pages, IEEE.

Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.

Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes in Computer Science, 2001, pp. 343-350, vol. 2208, Springer-Verlag.

Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.

Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.

Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.

Migga, Michael I. et al., "Intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.

Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.

Mitsuishi, Mamoru et al., "Remote Ultrasound Diagnostic System," Conf. on Robotics and Automation, 2001, pp. 1567-1574, vol. 2, IEEE.

Mourgues, Fabienet al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes in Computer Science, 2002, pp. 25-34, vol. 2488, Springer-Verlag.

Muratore, Diane M. et al., "Beam Calibration Without a Phantom for Creating a 3D Free-hand Ultrasound System," Ultrasound in Medicine and Biology, 2001, pp. 1557-1566, vol. 27—No. 11, Elsevier.

Nakakura, Eric K et al., "Hepatocellular Carcinoma: Current Management Recommendations," Advances on Oncology, 2000, pp. 12-18, vol. 16—No. 2.

Neisius B. et al., "Robotic manipulator for endoscopic handling of surgical effectors and cameras," 1st Intl. Symposium on Medical Robotics and Computer Assisted Surgery, 1994, pp. 169-176, vol. 2.

Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.

Nelson, Thomas, R. et al., "Three-dimensional ultrasound imaging," Ultrasound in Medicine & Biology, 1998, pp. 1243-1270, vol. 24—No. 9, Elsevier.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.

Novotny Paul M. et al., "Tool Localization in 3D Ultrasound Images," Medical Image Computing and Computer-Assisted Intervention, 2003, pp. 969-970, vol. 2879, Springer.

Office Action dated May 1, 2012 for Japanese Application No. 20090518470 filed Jun. 22, 2007, 7 pages.

Office Action dated Jan. 26, 2015 for Japanese Application No. 20130186992 filed Sep. 10, 2013, 9 pages.

(56) References Cited

OTHER PUBLICATIONS

Ohbuchi, Ryutarou et al., "Incremental Volume Reconstruction and Rendering for 3D Ultrasound Imaging," The International Society of Optical Engineering, 1992, pp. 312-323, vol. 1808, SPIE.

Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.

Patriciu Alexandru et al., "Motion-based robotic instrument targeting under c-arm fluoroscopy," Medical Image Computing and Computer-Assisted Interventions, 2000, pp. 988-998, vol. 1935, Springer.

Paul, Howard A. et al., "Development of a Surgical Robot for Cementless Total Hip Arthroplasty," Clinical Orthopaedics, Dec. 1992, pp. 57-66, vol. 285.

Podnos, Yale, D. et al., "Laparoscopic Ultrasound with Radiofrequency Ablation in Cirrhotic Patients with Hepatocellular Carcinoma," Am Surg, 2001, pp. 1181-1184, vol. 67—No. 12.

Poulose P. K et al., "Human vs Robotic Organ Retraction During Laparoscopic Nissen Fundoplication," Surgical Endoscopy, 1999, pp. 461-465, vol. 13, Springer-Verlag.

Prager Richard et al., "Practical segmentation of 3D ultrasound," In Proceedings of Medical Image Understanding and Analysis, 1999, pp. 161-164.

Prager Richard et al., "Rapid Calibration for 3D Freehand Ultrasound," Ultrasound in Medicine and Biology, 1998, pp. 855-869, vol. 24—No. 6, Elsevier.

Prasad, Srinivas K. et al., "A minimally invasive approach to pelvic osteolysis," 2002, in Proc. Computer-Assisted Orthopaedic Surgery (CAOS), pp. 349-350.

Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.

Preising, B. et al., "A Literature Review: Robots in Medicine," IEEE Engineering in Medicine and Biology, 1991, pp. 13-22, 71, vol. 10—Issue 2, IEEE.

Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.

Ramey, Nicholas A., "Stereo-Based Direct Surface Tracking with Deformable Parametric Models," 2003, 104 Pages Total.

Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

Ratner, Lloyd E. et al, "Laparoscopic live donor nephrectomy removes disincentives to live donation," Transplantation, 1997, pp. 3402-3403, vol. 29—Issue 8, Elsevier.

Ratner, Lloyd E. et al., "Laparoscopic live donor nephrectomy," Transplantation, 1995, pp. 1047-1049.

Rau, Beate, M. eta al., "Is There Additional Information From Laparoscopic Ultrasound in Tumor Staging", Digestive Surgery, 2002, pp. 479-483, vol. 19—No. 6.

Rockall, Timothy A., "The da Vinci Telerobotic Surgical System," Chapter 8 in Primer of Robotic & Telerobotic Surgery, Eds. Garth H. Ballantyne et al., Pub. By Lippincott Williams & Wilkins, Philadelphia, 2004, pp. 57-60.

Rohling, Robert et al., "Three-dimensional spatial compounding of ultrasound images," Medical Image Analysis, 1996, pp. 177-193, vol. 1—No. 3, Oxford University Press.

Rohling, Robert N. et al., "Radial basis function interpolation for 3-d ultrasound," CUED/F-INFENG/TR 327, Cambridge University, Jul. 1998, 28 Pages.

Rosen, Jacob et al., "The BlueDRAGON—A System for Measuring the Kinematics and the Dynamics of Minimally Invasive Surgical Tools In-Viva," Proceedings of the 2002 IEEE International Conference on Robotics 8 Automation, 2002, pp. 1876-1881, IEEE.

Rosenberg, Louis B., "Human interface hardware for virtual laparoscopic surgery," Proceedings of the Interactive Technology and the New Paradigm for Healthcare, 1995, pp. 322-325, Amsterdam: IOS Press.

Rosenberg, Louis B., "Virtual Fixtures: Perceptual Tools for Telerobotic Manipulation," IEEE Virtual Reality International Symposium, 1993, pp. 76-82, IEEE.

Rothbaum Daniel L. et al., "Robot-assisted stapedotomy: micropick fenestration of the stapes footplate," Otolaryngology—Head and NeckSurgery, 2002, pp. 417-426, vol. 127.

Rothbaum Daniel L. et al., "Task Performance in stapedotomy: Comparison between surgeons of different experience levels," Otolaryngology—Head and Neck Surgery, 2003, pp. 71-77, vol. 128—No. 1.

Roy, Jaydeep, "Advances in the design, analysis and control of force controlled robots," Master's Thesis, Mechanical Engineering, Johns Hopkins University, Baltimore, 2001, 210 Pages.

Sakas, Georgios et al., "Extracting surfaces from fuzzy 3D-Ultrasound data," Proceedings of the 22nd annual conference on Computer graphics and interactive techniques, 1995, pp. 465-474.

Salcudean, Septimiu E. et al., "A Robot System for Medical Ultrasound," 9th International Symposium of Robotics Research (ISRR'99), 1999, pp. 195-202.

Santambrogio, R. et al., "Ultrasound-Guided Interventional Procedures of the Liver During Laparoscopy: Technical Considerations," Surg Endosc, 2002, pp. 349-354, Springer-Verlag.

Sastry, Shankar et al., "Millirobotics for remote minamally invasive surgery," Proceedings of the Intl. Workshop on Some Critical Issues in Robotics, Singapore, Oct. 2-3, 1995, pp. 81-98.

Sastry, Shankar, http://robotics.eecs.berkeley.edu, Nov. 1, 1995, Total 8 pages.

Sastry, Shankar, "MilliRobotics in Minimally Invasive Telesurgery," Internet, http://robotics.eecs.berkeley.edu, 1996, 8 pages.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Schorr, Oliver et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes in Computer Science, 2000, pp. 979-978, vol. 1935, Springer.

Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.

Schweikard, Achim et al., "Motion Planning in Stereotaxic Radiosurgery," IEEE Transactions on Robotics and Automation, 1993, pp. 909-916, vol. 1, IEEE.

Scott, D.J., "Accuracy and Effectiveness of Laparoscopic vs. Open Hepatic Radiofrequency Ablation," Surg Endosc, 2001, pp. 349-354, vol. 16—No. 2, Springer.

Shahram, Payandeh, et al., "On Application of Virtual Fixtures as an Aid for Telemanipulation and Training," IEEE 10th Symposium on Haptic Interfaces for Virtual Environment and Teleoperator systems, Mar. 24-25, 2002, pp. 18-23, IEEE.

Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.

Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.

Solomon, Stephen B. et al., "CT Guided Robotic Needle Biopsy: A Precise Sampling Method Minimizing Radiation Exposure to the Physician, Radiology," 2002, pp. 277-282, vol. 225.

Solomon, Stephen B. et al., "Robotically Driven Interventions: A Method of Using CT Fluoroscopy without Radiation Exposure to the Physician," Radiology, 2002, pp. 277-282, vol. 225.

(56) References Cited

OTHER PUBLICATIONS

SOLUS-3D web site: Last updated Jun. 24, 1999; downloaded Jul. 5, 2007.

Sommer, Graham et al., "Liver tumors: utility of characterization at dual frequency US," Radiology, 1999, pp. 629-636, vol. 211—No. 3.

Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.

Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.

Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.

Stetten, George D et al., "Overlaying Ultrasound Images on Direct Vision," Journal of Ultrasound in Medicine, 2001, pp. 235-240, vol. 20—No. 3.

Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.

Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag.

Stoianovici, Dan et al., "Robotic for Precise Percutaneous Needle Insertion," In Thirteenth Annual Meeting of the Society for Urology and Engineering. San Diego, May 1998, pp. 4.

Stoianovici, Dan et al., "Robotic Telemanipulation for Percutaneous Renal Access," 16th World Congress on Endourology, 1998, pp. S201.

Stoll, Jeff, "Ultrasound-based servoing of manipulators for telesurgery," Telemanipulator and Telepresence Technologies VIII Conference, 2001, pp. 78-85, SPIE.

Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.

Suramo, I. et al., "Cranio-caudal movements of the liver, pancreas and kidneys in respiration," Acta Radiologica: Diagnosis, 1984, pp. 129-131, vol. 25, Radiological Societies.

Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.

Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.

Taubes, Gary et al., "Surgery in Cyberspace," Discover magazine, Dec. 1994, vol. 15, issue 12, pp. 85-92.

Tavakoli, M., et al, A Force Reflective Master-Slave System for Minimally Invasive Surgery, Proc. IEEE/RSJ International Conference on Intelligent Robots and Systems, 2003, pp. 3077-3082, vol. 4, IEEE.

Taylor, Russell H., "A Perspective on Medical Robotics," Proceedings of the IEEE, vol. 94, No. 9, Sep. 2006, pp. 1652-1664.

Taylor, Russell H. "An Image-directed Robotic System for Precise Orthopaedic Surgery," IEEE Transactions on Robotics mid Automation, 1994, pp. 261-275, vol. 10—No. 3, IEEE.

Taylor, Russell H. and Christopher Hasser, "Development of a Surgical Assistant Workstation for Teleoperated Surgical Robots," NSF Proposal No. 0646678, Aug. 2006, 16 pages.

Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.

Taylor, Russell H. and Peter Kazanzides, "Medical Robotics and Computer-Integrated Interventional Medicine," Chapter 18: Biomedical Information Technology, David Dagan Feng, Ed., Academic Press (Elsevier), 2008, pp. 393-416.

Taylor, Russell H. et al., "A Computational Architecture for Programmable Automation Research," Conference on Intelligent Robots and Computer Vision, 1986, pp. 438-440, vol. 726, SPIE.

Taylor, Russell H. et al., "A General Purpose Control Architecture for Programmable Automation Research," Proceedings of the Third International Symposium on Robotics, 1986, pp. 165-174, MIT Press.

Taylor, Russell, H et al., "A Steady-Hand Robotic System for Microsurgical Augmentation," International Journal of Robotics Research, 1999, pp. 1201-1210, vol. 18—No. 12, Springer-Verlag.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "A Telerobotic System for Augmentation of Endoscopic Surgery," in IEEE Conference on Engineering in Medicine and Biology, vol. 14, 1992, pp. 1054-1056, vol. 3, IEEE.

Taylor, Russell, H et al., "AML A Manufacturing Language," The International Journal of Robotics Research, 1982, pp. 19-41, vol. 1—No. 3, Sage Publications.

Taylor, Russell H. et al., "An Image-directed Robotic System for Hip Replacement Surgery," J. Robotics Society of Japan, 1990, pp. 615-620, vol. 8—issue 5.

Taylor, Russell, H. et al., "An Integrated Robot Systems Architecture," Proceedings of the IEEE, 1983, pp. 842-856, vol. 71—Issue 7, IEEE.

Taylor, Russell H., et al., "An overview of computer-integrated surgery at the IBM Thomas J. Watson Research Center," IBM J Research and Development, 1996, pp. 163-183, vol. 40, Issue 2, IBM Corp.

Taylor, Russell H., et al., "Chapter 46: A Telerobotic Assistant for Laparoscopic Surgery," in Computer-Integrated Surgery, R. H. Taylor, et al., Editors, 1996, MIT Press. pp. 581-592.

Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.

Taylor, Russell H. et al., "Computer-Integrated Surgery," 1996, 8 Pages, MIT Press.

Taylor, Russell H. et al., "Medical Robotics and Computer-Integrated Surgery," Chapter 52 in Springer Handbook of Robotics, Springer, 2008, pp. 1199-1222.

Taylor, Russell H. et al., "Medical Robotics in Computer-Integrated Surgery," IEEE Transactions on Robotics md Automation, 2003, pp. 765-781, vol. 19—No. 5, IEEE.

Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.

Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.

Taylor, Russell, H et al., "The Architecture of an Integrated Robot System," First Int. Conf. on Advanced Robotics (ICAR)., 1983, pp. 389-398.

Taylor, Russell H. "Medical Robotics and Computer-Integrated Surgery," Handbook of Industrial Robotics, Second Edition, 1999, pp. 1213-1230, Chapter 65, John Wiley & Sons.

Taylor, Russell H. "Medical Robots," in Computer and Robotic Assisted Knee and Hip Surgery, 2004, pp. 54-59, Oxford Press.

Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.

Taylor, Russell H. "The Planning and Execution of Straight Line Manipulator Trajectories," IBM Journal of Research and Development, 1979, pp. 424-436, vol. 23—Issue 4.

(56) References Cited

OTHER PUBLICATIONS

Taylor, Russell H., "Ultrasound Assistant for a Laparoscopic Surgical Robot," NIH STTR Phase II Proposal R42-RR019159, revised May 2001, 54 pages.
Taylor, Russell H., Videotape: "Computer Assisted Surgery at IBM T. J. Watson Research Center," 22 minutes 10 seconds, 1994 and 1995.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572,vol. 60—No. 4, Elsevier.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Toon, John, "Virtual Reality for Eye Surgery," Georgia Tech Research News, 1993, 4 Pages.
Toyama, Kentaro et al., "Incremental Focus of Attention for Robust Visual Tracking," International Journal of Computer Vision, 1999, pp. 45-63, vol. 35—No. 1, Kluwer Academic Publishers.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Trivedi, Mohan M. et al., "Developing telerobotic systems using virtual reality concepts," 1993 IEEE/RSJ International Conference on Intelligent Robots and systems, 1993, pp. 352-359, vol. 1, IEEE.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Uecker, Darrin R. et al., "A Speech-Directed Multi-Modal Man-Machine Interface for Robotically Enhanced Surgery," 1994, pp. 176-183.
Umeyama, Shinji, "Least-Squares Estimation of Transformation Parameters between Two Point Patterns," IEEE Transactions on Pattern Analysis and Machine Intelligence (PAMI), vol. 13, No. 4, pp. 376-380, Apr. 1991.
U.S. Appl. No. 11/583,963 Non-Final Office Action dated Jul. 9, 2009, 40 pages.
Vibet, C., "Properties of Master Slave Robots," Motor-con, 1987, pp. 309-316.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster Robert J. et al., "Design Considerations for Robotic Needle Steering," International Conference on Robotics and Automation, 2005, pp. 3588-3594, IEEE.
Webster Robert J. et al "Nonholonomic Modeling of Needle Steering," The International Journal of Robotics Research, 2004, pp. 509-525, vol. 25—No. 5-6, Sage Publications.
Wei, Zhouping et al "Robot-assisted 3D-TRUS guided prostate brachytherapy: system integration and validation," Medical Physics, 2004, pp. 539-548, vol. 31—No. 3.
Wengert, Christian, "Camera Calibration Toolbox for Matlab," 5 pages.
Wilhelm, Dirk et al., "Electromagnetically Navigated Laparoscopic Ultrasound," Surg. Technol. Int, 2003, pp. 50-54, vol. 11.
Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.
Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.
Xu, Sheng et al., "3D Motion Tracking of Pulmonary Lesions Using CT Fluoroscopy Images for Robotically Assisted Lung Biopsy," International Society of Optical Engineering, 2004, pp. 394-402, SPIE.
Yamagata, Hitoshi, "Development of a New Display Method for Compound 3D Ultrasound Images: Fusion 3D Images From B-mode and 3D Doppler Images," 1999, pp. 43-46, vol. 70.
Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.
Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.
Yao, Jianhua et al., "Deformable registration between a statistical born density atlas and X-ray images," Second International Conference on Computer Assisted Orthopaedic Surgery, 2002, pp. 168-169.
Zacherl, Johannes et al., "Current value of intraoperative sonography during surgery for hepatic neoplasms," World J Surg, 2002, pp. 550-554, vol. 26—No. 5.
Zhang, Zhengyou, "A Flexible New Technique for Camera Calibration," 1998, pp. 1-21.
Pose—definition from Merriam Webster Dictionary, 4 pages, [online], [retrieved on Apr. 3, 2015]. Retrieved from the Internet: <URL: http://www.merriam-webster.com/dictonary/pose>.
Posture—definition from Merriam Webster Dictionary, 4 pages, [online], [retrieved on Apr. 3, 2015]. Retrieved from the Internet: <URL: http://www.merriam-webster.com/dictonary/posture>.
Office Action dated May 7, 2015 for European Application No. 20090770698 filed Jun. 4, 2009, 5 pages.
Herper Matthew, "Watch a $1.5 Million Surgical Robot Play a Board Game," Forbes. Apr. 12, 2011. 2 pages, Online [Available: http://www.forbes.com/sites/matthewherper/2011/04/12/watch-a-1-5-million-surgical-robot-play-a-board-game/#587224f011f5] Accessed Jun. 7, 2016.
Office Action dated May 9, 2016 for Chinese Application No. 201410779062.7 filed Jun. 4, 2009, 13 pages.
Cleary, Kevin et al., "State of the Art in Surgical Robotics:Clinical Applications and Technology Challenges," Computer Aided Surgery, 2001 [retrieved on Feb. 24, 2002], pp. 1-26.
Ganssle J.G.,, "A Guide to Debouncing", The Ganssle Group, Jun. 2008, 26 pages.
Office Action dated Jun. 12, 2015 for Japanese Application No. 20130186992 filed Sep. 10, 2013, 8 pages.
Bettini , A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.
Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.
International Search Report and Written Opinion for Application No. PCT/US2012/064379, dated Mar. 29, 2013, 12 pages.
International Search Report and Written Opinion for Application No. PCT/US2012/064400, dated Mar. 27, 2013, 10 pages.
Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.
PCT/US09/56078 International Search Report and Written Opinion of the International Searching Authority, dated Jan. 20, 2010, 12 pages.

(56) References Cited

OTHER PUBLICATIONS

PCT/US10/28886 International Search Report and Written Opinion of the International Searching Authority, dated Jul. 6, 2010, 11 pages.
PCT/US2011/036109 International Search Report and Written Opinion of the International Searching Authority, dated Oct. 19, 2011, 16 pages.
PCT/US2011/036109 Invitation to Pay Additional Fees and Partial International Search Report, dated Aug. 18, 2011, 5 pages.
Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.
Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.
Office Action dated Sep. 3, 2014 for Japanese Application No. JP20120503535 filed Mar. 26, 2010.
Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.
Kato H., et al., "The Effects of Spatial Cues in Augmented Reality Video Conferencing," Hiroshima City University, Aug. 2001, 4 pages.
Kato H., et al. "Virtual Object Manipulation on a Table-Top AR Environment," Hiroshima City University, 2000, 9 pages.
Office Action dated Dec. 15, 2015 for Korean Application No. 10-2010-7027491 filed Dec. 7, 2010, 14 pages.
Office Action dated Dec. 16, 2016 for Japanese Application No. 2015242062 filed Oct. 14, 2015, 13 pages.
Stoainovici D., et al., "Robotic Telemanipulation for Percutaneous Renal Access," in 16th World Congress on Endourology, New York City, Sep. 3-6, 1998, Poster Session 17-5, p. S201.
Azuma et al., "Recent Advances in Augmented Reality," IEEE Computer Graphics and Applications, Dec. 2001, 14 pages.
Lievin et al., "Stereoscopic Augmented Reality System for Computer Assisted Surgery," CARS 2001, Jun. 27-30, 2001, pp. 34-47.
Extended European Search Report for Application No. EP18158957. 3, dated Jun. 25, 2018, 8 pages.

* cited by examiner

MEDICAL ROBOTIC SYSTEM PROVIDING AN AUXILIARY VIEW OF ARTICULATABLE INSTRUMENTS EXTENDING OUT OF A DISTAL END OF AN ENTRY GUIDE

FIELD OF THE INVENTION

The present invention generally relates to medical robotic systems and in particular, to a medical robotic system providing an auxiliary view of articulatable instruments extending out of a distal end of an entry guide.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulatable camera and a plurality of articulatable surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

Since the entry guide generally has a relatively small diameter in order to fit through a minimally invasive incision or a natural body orifice, a number of problems may arise while teleoperating the surgical tools to perform the medical procedure and the camera to view it. For example, because the camera is bundled with the surgical tools, it is limited in its positioning relative to the surgical tools and consequently, its view of the surgical tools.

Thus, although the tips of the articulatable surgical tools may be kept in the field of view of the camera, controllable linkages which facilitate the articulatability of the surgical tools may not be in the field of view of the camera. As a consequence, the controllable linkages of the surgical tools may inadvertently collide with each other (or with a link of the camera) during the performance of a medical procedure and as a result, cause harm to the patient or otherwise adversely impact the performance of the medical procedure.

Also, since the articulatable camera is generally incapable of viewing its own controllable linkage, operator movement of the camera is especially a concern where collisions with the surgical tool links are to be avoided. Further, when intuitive control is provided to assist the operator in teleoperatively moving the surgical tools and camera, the motions of the linkages required to produce such intuitive motions of the tips of the tools and camera may not be obvious or intuitive to the operator, thus making it even more difficult for the operator to avoid collisions between linkages that are outside the field of view of the camera.

OBJECTS AND SUMMARY OF THE INVENTION

Accordingly, one object of one or more aspects of the present invention is a method that provides an auxiliary view to an operator to assist the operator in performing a medical procedure on a patient using a medical robotic system having articulatable instruments extending out of a distal end of an entry guide inserted through a single entry aperture in the patient.

Another object of one or more aspects of the present invention is a method implemented in such a medical robotic system that provides a visual indication to an operator that indicates when controllable linkages of the articulatable instruments may collide.

Another object of one or more aspects of the present invention is a method implemented in a medical robotic system that provides a visual indication to an operator that indicates when joints and/or links and/or portions thereof of the articulatable instruments are nearing an undesirable or desirable event or condition.

Another object of one or more aspects of the present invention is a method implemented in such a medical robotic system that improves an operator's understanding of the configuration of the linkages of the articulatable instruments that are outside of the field of view of a camera.

These and additional objects are accomplished by the various aspects of the present invention, wherein briefly stated, one aspect is a method for providing a computer generated view, comprising: receiving information of states of one or more articulatable instruments extending out of a distal end of an entry guide; generating a view using the received information and forward kinematics of the one or more articulatable instruments; and displaying the generated view on a display screen.

Another aspect is a medical robotic system comprising: an entry guide; a plurality of instruments extending through and out of a distal end of the entry guide; a plurality of sensors adapted to sense states of articulating elements of the plurality of instruments; a display screen; and a controller configured to receive information including the sensed states of the articulating elements from the plurality of sensors, generate a view using the received information, and display the generated view on the display screen.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
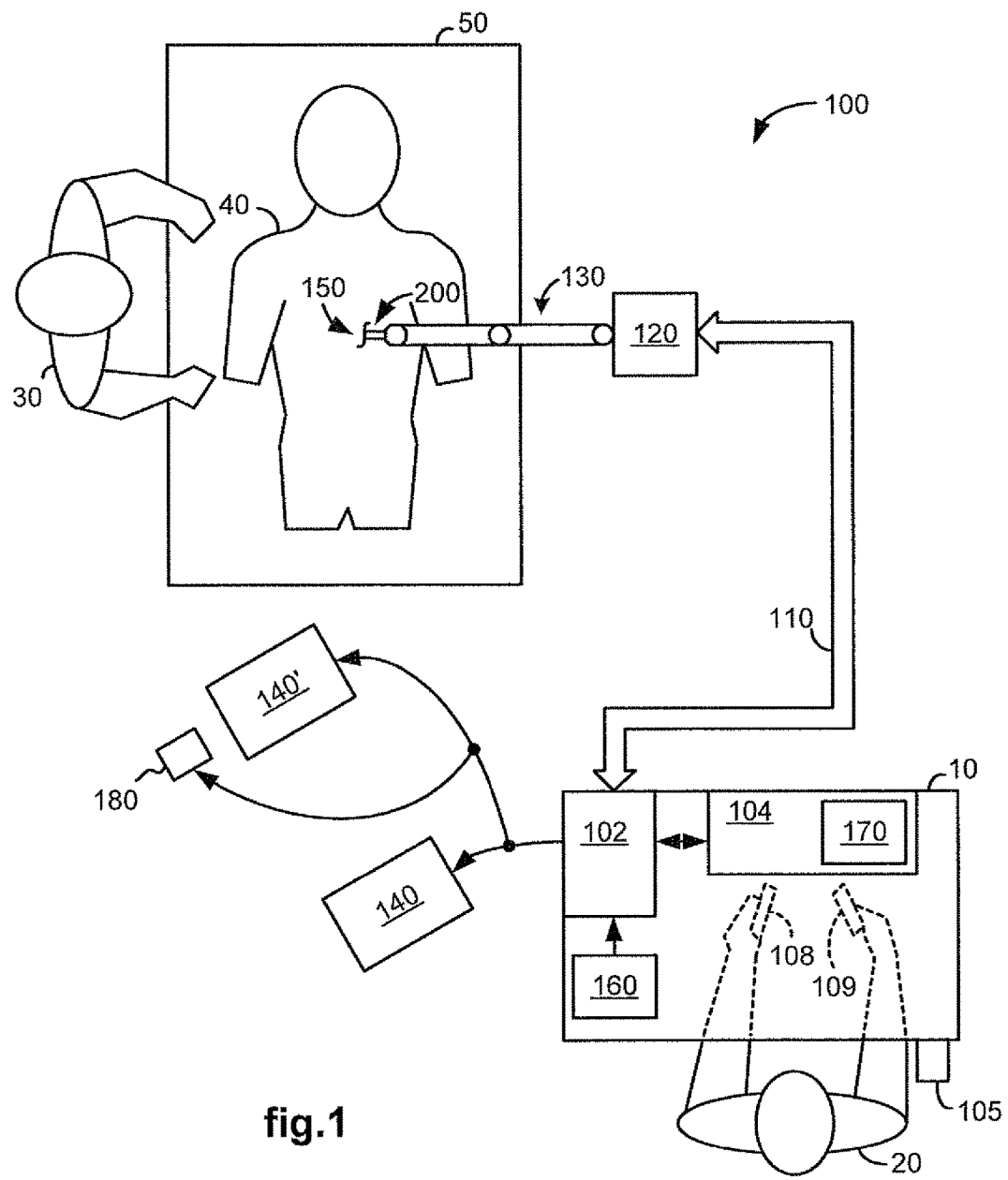
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130 that is mounted to a support 120.

Figure 5:
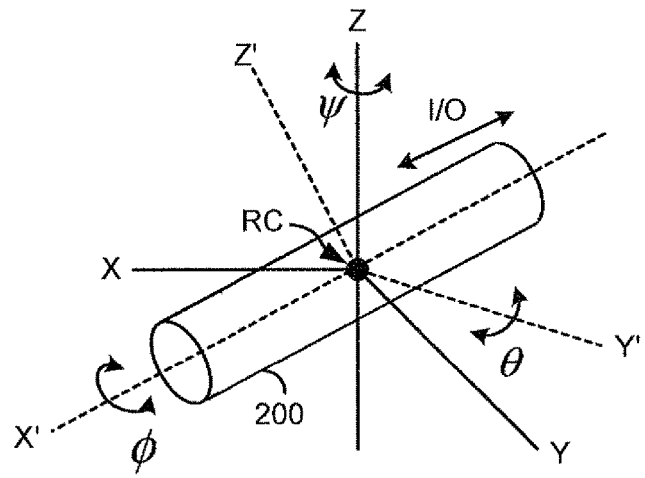
FIG. 5 illustrates a perspective view of an entry guide and its four degrees-of-freedom movement as used in a medical robotic system utilizing aspects of the present invention.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. An example of such an entry guide manipulator is the entry guide manipulator 202 of FIG. 2 and an example of the four degrees-of-freedom movement that it manipulates the entry guide 200 with is shown in FIG. 5.

The console 10 includes a 3-D monitor 104 for displaying a 3-D image of a surgical site to the Surgeon, left and right hand-manipulatable input devices 108, 109, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

An auxiliary display screen 140 is coupled to the console 10 (and processor 102) for providing auxiliary views to the Surgeon to supplement those shown on the monitor 104. A second auxiliary display screen 1401 is also coupled to the console 10 (and processor 102) for providing auxiliary views to the Assistant(s). An input device 180 is also coupled to the console to allow the Assistant(s) to select between available auxiliary views for display on the second auxiliary display screen 140'.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures. In such a case, the console 10 may be connected to the second auxiliary display screen 140' and input device 180 through a network connection such as a local area network, wide area network, or the Internet.

Figure 3:
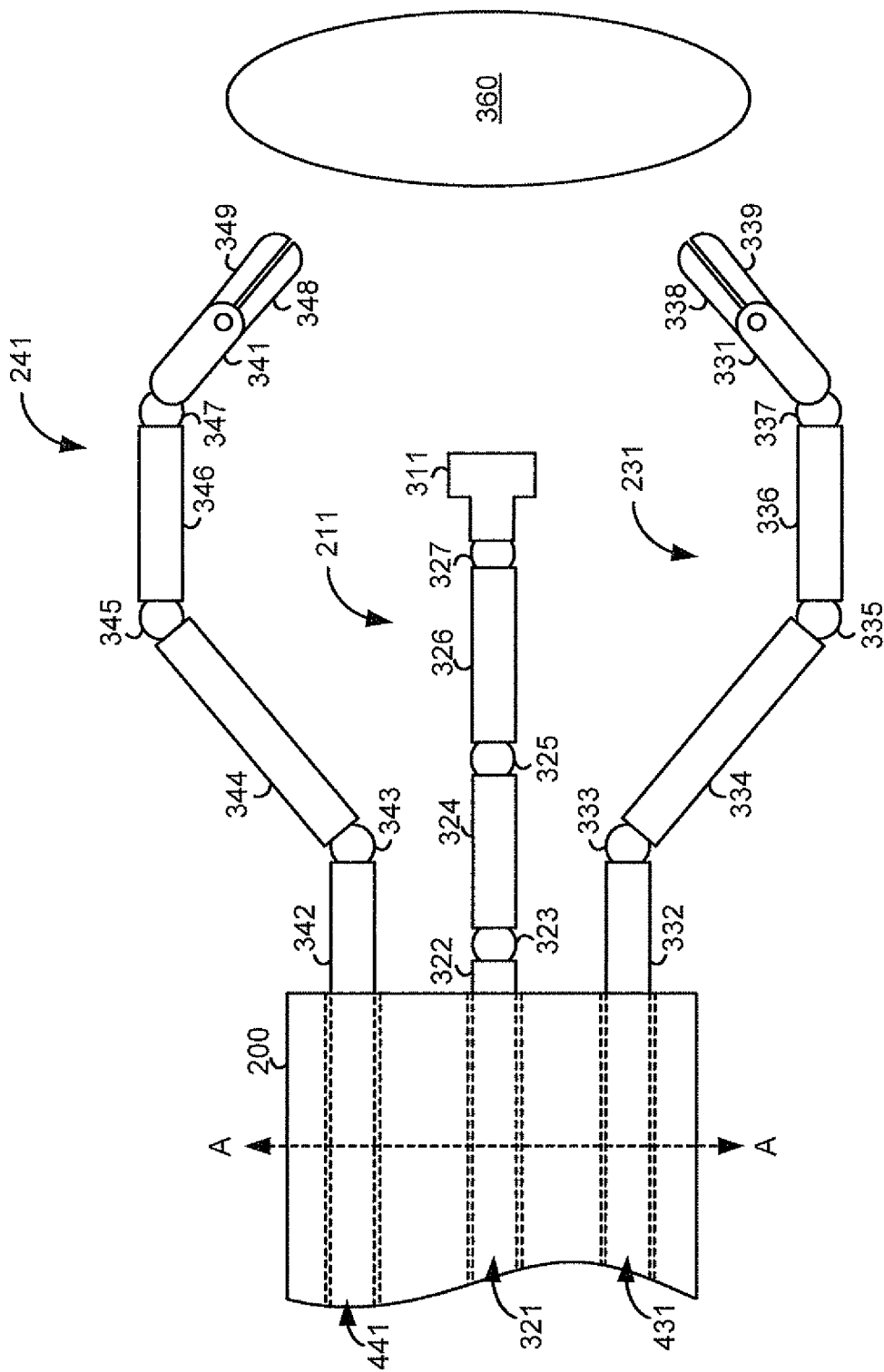
FIGS. 3-4 respectively illustrate top and side views of an articulatable camera and a pair of articulatable surgical tools extending out of a distal end of an entry guide as used in a medical robotic system utilizing aspects of the present invention.
Figure 4:
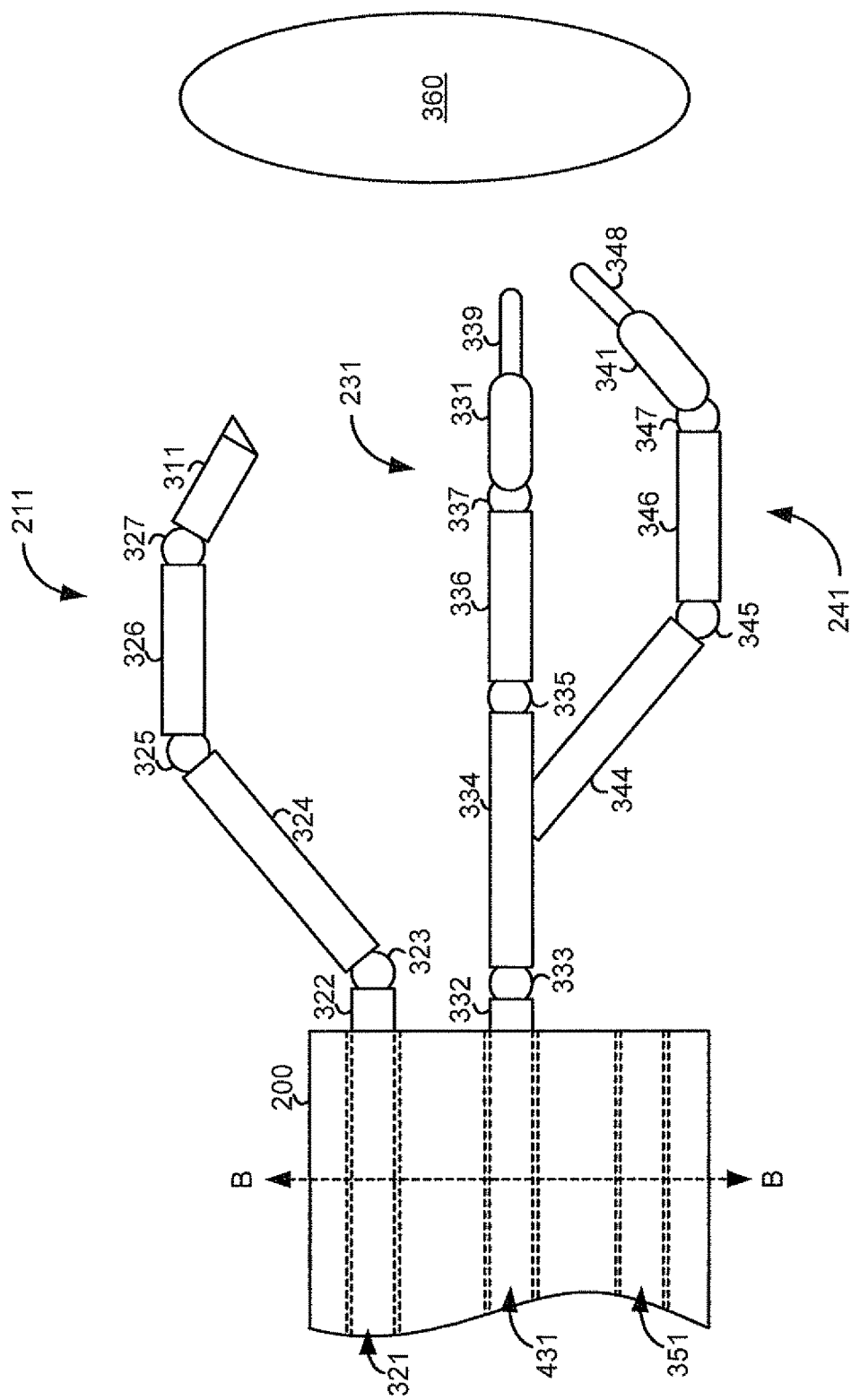

As shown in FIGS. 3-4, the entry guide 200 has articulatable instruments such as articulatable surgical tools 231, 241 and an articulatable stereo camera 211 extending out of its distal end. Although only two tools 231, 241 are shown, the entry guide 200 may guide additional tools as required for performing a medical procedure at a work site in the Patient. For example, as shown in FIG. 4, a passage 351 is available for extending another articulatable surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the articulatable camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 may transform the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and controller functions described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
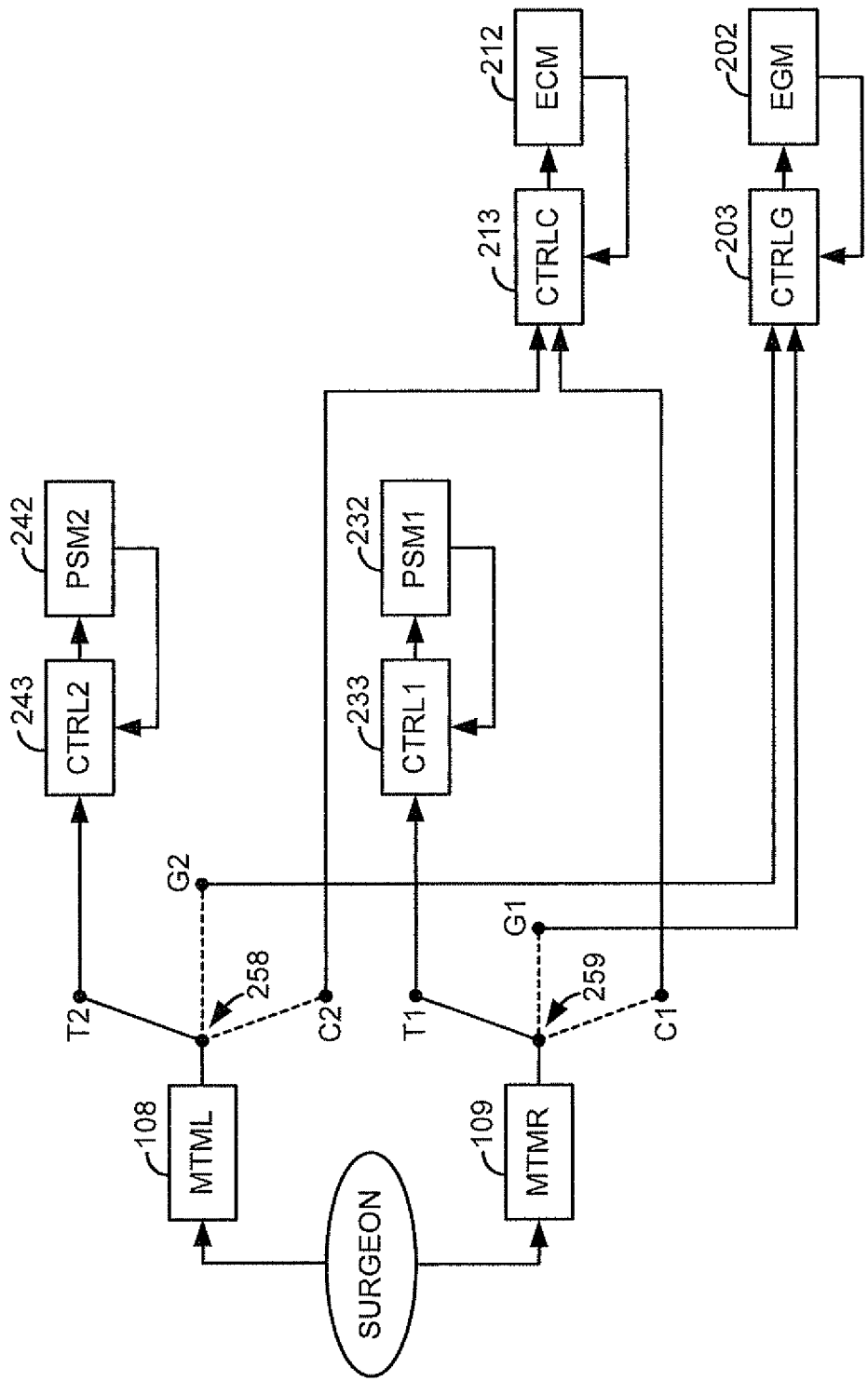
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202. So as to not overly encumber the figure, the devices 231, 241, 211, 200 are not shown, only their respective manipulators 232, 242, 212, 202 are shown in the figure.

Each of the instrument manipulators 232, 242, 212 is a mechanical assembly that carries actuators and provides a mechanical, sterile interface to transmit motion to its respective articulatable instrument. Each instrument 231, 241, 211 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

In contrast, the entry guide manipulator 202 has a different construction and operation. A description of the parts and operation of the entry guide manipulator 202 is described below in reference to FIG. 7.

In this example, each of the input devices 108, 109 may be selectively associated with one of the devices 211, 231, 241, 200 so that the associated device may be controlled by the input device through its controller and manipulator. For example, by placing switches 258, 259 respectively in tool following modes "T2" and "T1", the left and right input devices 108, 109 may be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the entry guide 200 is locked in place.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller. For example, by placing switches 258, 259 respectively in camera positioning modes "C2" and "C1", the left and right input devices 108, 109 may be associated with the camera 211, which is telerobotically controlled through its controller 213 (preferably implemented in the processor 102) and manipulator 212 so that the Surgeon may position the camera 211 while the surgical tools 231, 241 and entry guide 200 are locked in place by their respective controllers 233, 243, 203. If only one input device is to be used for positioning the camera, then only one of the switches 258, 259 is placed in its camera positioning mode while the other one of the switches 258, 259 remains in its tool following mode so that its respective input device may continue to control its associated surgical tool.

On the other hand, by placing switches 258, 259 respectively in entry guide positioning modes "G2" and "G1", the left and right input devices 108, 109 may be associated with the entry guide 200, which is telerobotically controlled through its controller 203 (preferably implemented in the processor 102) and manipulator 202 so that the Surgeon may position the entry guide 200 while the surgical tools 231, 241 and camera 211 are locked in place relative to the entry guide 200 by their respective controllers 233, 243, 213. As with the camera positioning mode, if only one input device is to be used for positioning the entry guide, then only one of the switches 258, 259 is placed in its entry guide positioning mode while the other one of the switches 258, 259 remains in its tool following mode so that its respective input device may continue to control its associated surgical tool.

The selective association of the input devices 108, 109 to other devices in this example may be performed by the Surgeon using the GUI 170 or the voice recognition system 160 in a conventional manner. Alternatively, the association of the input devices 108, 109 may be changed by the Surgeon depressing a button on one of the input devices 108, 109 or depressing the foot pedal 105, or using any other well known mode switching technique.

FIGS. 3-4 respectively illustrate, as examples, top and right side views of a distal end of the entry guide 200 with the camera 211 and surgical tools 231, 241 extending outward. As shown in a perspective view of a simplified (not to scale) entry guide 200 in FIG. 5, the entry guide 200 is generally cylindrical in shape and has a longitudinal axis X' running centrally along its length. The pivot point, which is also referred to as a remote center "RC", serves as an origin for both a fixed reference frame having X, Y and Z axes as shown and an entry guide reference frame having X', Y' and Z' axes as shown. When the system 100 is in the entry guide positioning mode, the entry guide manipulator 202 is capable of pivoting the entry guide 200 in response to movement of one or more associated input devices about the Z axis (which remains fixed in space) at the remote center "RC" in yaw ψ. In addition, the entry guide manipulator 202 is capable of pivoting the entry guide 200 in response to movement of the one or more input devices about the Y' axis (which is orthogonal to the longitudinal axis X' of the entry guide 200) in pitch θ, capable of rotating the entry guide 200 about its longitudinal axis X' in roll Φ, and linearly moving the entry guide 200 along its longitudinal axis X' in insertion/retraction or in/out "I/O" directions in response to movement of the one or more associated input devices. Note that unlike the Z-axis which is fixed in space, the X' and Y' axes move with the entry guide 200.

Figure 7:
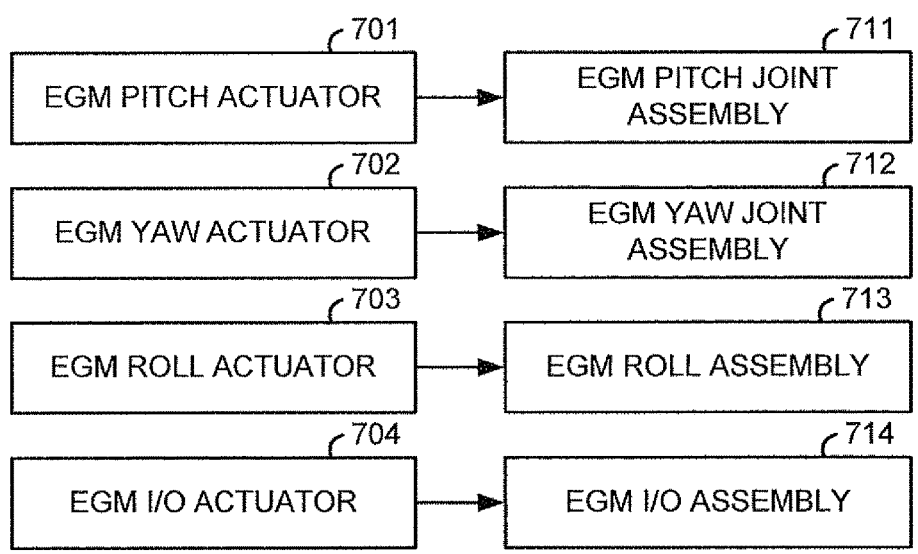
FIG. 7 illustrates a block diagram of interacting components of an entry guide manipulator as used in a medical robotic system utilizing aspects of the present invention.

As shown in FIG. 7, the entry guide manipulator (ESM) 202 has four actuators 701-704 for actuating the four degrees-of-freedom movement of the entry guide 200 (i.e., pitch θ, yaw ψ, roll Φ, and in/out I/O) and four corresponding assemblies 711-714 to implement them.

Referring back to FIGS. 3-4, the articulatable camera 211 extends through passage 321 and the articulatable surgical tools 231, 241 respectively extend through passages 431, 441 of the entry guide 200. The camera 211 includes a tip 311 (which houses a stereo camera connected to a camera controller and a fiber-optic cable connected to an external light source), first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 8 (plus an additional actuator for actuating the end effector 331). Likewise, the tool 241 includes an end effector 341 (having jaws 348, 349), first, second, and third links 342, 344, 346, first and second joint assemblies 343, 345, and a wrist assembly 347 that are also driven by actuators such as described in reference to FIG. 8 (plus an additional actuator for actuating the end effector 341).

Figure 8:
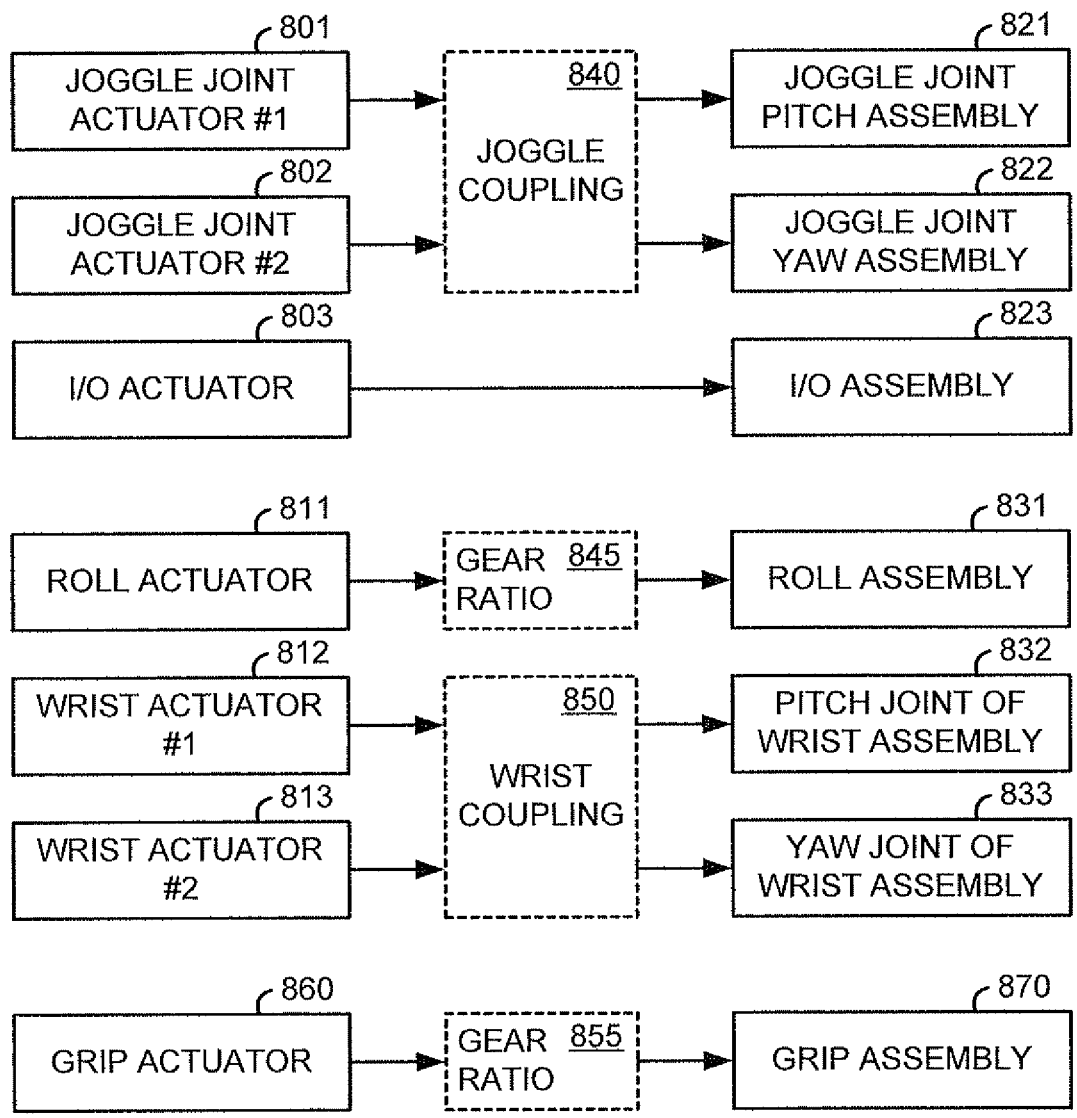
FIG. 8 illustrates a block diagram of interacting components of an articulatable instrument manipulator and an articulatable instrument as used in a medical robotic system utilizing aspects of the present invention.

FIG. 8 illustrates, as an example, a diagram of interacting parts of an articulatable instrument (such as the articulatable camera 211 and the articulatable surgical tools 231, 241) and its corresponding instrument manipulator (such as the camera manipulator 212 and the tool manipulators 232, 242). Each of the instruments includes a number of actuatable assemblies 821-823, 831-833, 870 for effectuating articulation of the instrument (including its end effector), and its corresponding manipulator includes a number of actuators 801-803, 811-813, 860 for actuating the actuatable assemblies.

In addition, a number of interface mechanisms may also be provided. For example, pitch/yaw coupling mechanisms 840, 850 (respectively for the joggle joint pitch/yaw and the wrist pitch/yaw) and gear ratios 845, 855 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 840, the coupling between the joggle joint actuators 801, 802 (differentiated as #1 and #2) and joggle joint pitch/yaw assemblies 821, 822 may include a pair of coupling mechanisms—one on each side of the sterile interface (i.e., one on the manipulator side of the interface and one on the instrument side of the interface).

Likewise, although shown as a single block 850, the coupling between the wrist actuators 812, 813 (differentiated as #1 and #2) and wrist pitch/yaw joint assemblies 832, 833 may also comprise a pair of coupling mechanisms—one on each side of the sterile interface.

Both the joggle joint pitch assembly 821 and the joggle joint yaw assembly 822 share the first, second and third links (e.g., links 322, 324, 326 of the articulatable camera 211) and the first and second joints (e.g., joints 322, 325 of the articulatable camera 211). In addition to these shared components, the joggle joint pitch and yaw assemblies 821, 822 also include mechanical couplings that couple the first and second joints (through joggle coupling 840) to the joggle joint pitch and yaw actuators 801, 802 so that the second link may controllably pivot about a line passing through the first joint and along an axis that is latitudinal to the longitudinal axis of the first link (e.g., link 322 of the articulatable camera 211) and the second link may controllably pivot about a line passing through the first joint and along an axis that is orthogonal to both the latitudinal and longitudinal axes of the first link.

The in/out (I/O) assembly 823 includes the first link (e.g., link 322 of the articulatable camera 211) and interfaces through a drive train coupling the in/out (I/O) actuator 803 to the first link so that the first link is controllably moved linearly along its longitudinal axis by actuation of the I/O actuator 803. The roll assembly 831 includes the first link and interfaces through one or more gears (i.e., having the gear ratio 845) that couple a rotating element of the roll actuator 811 (such as a rotor of a motor) to the first link so that the first link is controllably rotated about its longitudinal axis by actuation of the roll actuator 811.

The instrument manipulator (e.g., camera manipulator 212) includes wrist actuators 812, 813 that actuate through wrist coupling 850 pitch and yaw joints 832, 833 of the wrist assembly (e.g., wrist 327 of the articulatable camera 211) so as to cause the instrument tip (e.g., camera tip 311) to controllably pivot in an up-down (i.e., pitch) and side-to-side (i.e., yaw) directions relative to the wrist assembly. The grip assembly 870 includes the end effector (e.g., end effector 331 of the surgical tool 231) and interfaces through one or more gears (i.e., having the gear ratio 855) that couple the grip actuator 860 to the end effector so as to controllably actuate the end effector.

Figure 9:
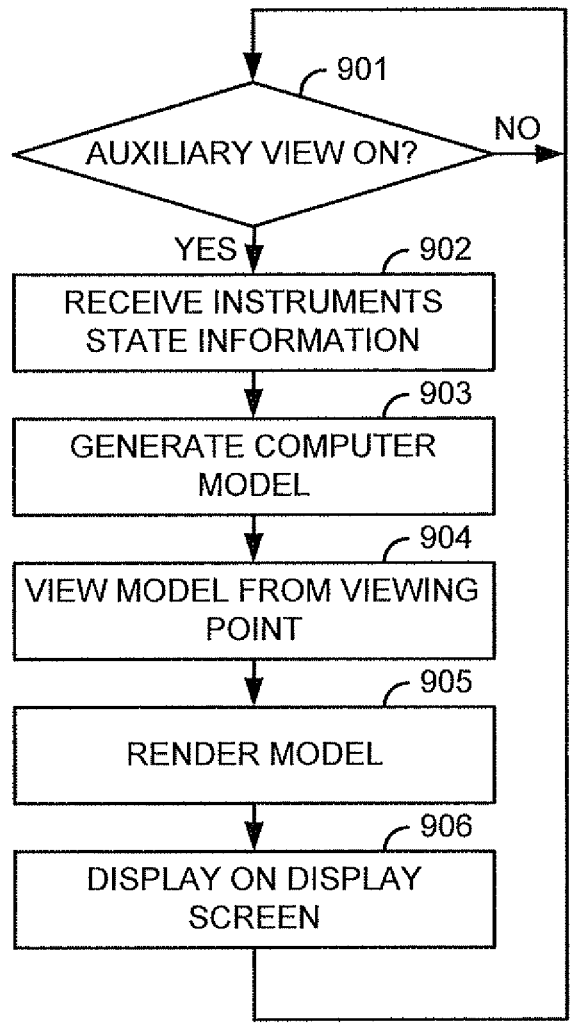
FIG. 9 illustrates a flow diagram of a method for providing a computer generated auxiliary view, utilizing aspects of the present invention.

FIG. 9 illustrates, as an example, a flow diagram of a method implemented in controller 102 of the medical robotic system 100 for providing a computer generated auxiliary view including articulatable instruments, such as the articulatable camera 211 and/or one or more of the articulatable surgical tools 231, 241, extending out of the distal end of the entry guide 200. For the purposes of this example, it is assumed that the articulatable camera 211 and surgical tools 231, 241 extend out of the distal end of the entry guide 200 and are included in the auxiliary view. However, it is to be appreciated that the method is applicable to any combination of articulatable instruments, including those without an articulatable camera and/or those with an alternative type of image capturing device such as an ultrasound probe.

In 901, the method determines whether or not an auxiliary view is to be generated. If the determination in 901 is NO, then the method loops back to periodically check to see whether the situation has changed. On the other hand, if the determination in 901 is YES, then the method proceeds to 902. The indication that an auxiliary view is to be generated may be programmed into the controller 102, created automatically or created by operator command.

In 902, the method receives state information, such as positions and orientations, for each of the instruments 211, 231, 241 and the entry guide 200. This information may be provided by encoders coupled to the actuators in their respective manipulators 212, 232, 242, 202. Alternatively, the information may be provided by sensors coupled to joints and/or links of the instruments 211, 231, 241 and the entry guide manipulator 202, or the coupling mechanisms, gears and drive trains of the interface between corresponding manipulators and instruments, so as to measure their movement. In this second case, the sensors may be included in the instruments 211, 231, 241 and entry guide manipulator 202 such as rotation sensors that sense rotational movement of rotary joints and linear sensors that sense linear movement of prismatic joints in the instruments 211, 231, 241 and entry guide manipulator 202. Other sensors may also be used for providing information of the positions and orientations of the instruments 211, 231, 241 and entry guide 200 such as external sensors that sense and track trackable elements, which may be active elements (e.g., radio frequency, electromagnetic, etc.) or passive elements (e.g., magnetic, etc.), placed at strategic points on the instruments 211, 231, 241, the entry guide 200 and/or the entry guide manipulator 202 (such as on their joints, links and/or tips).

In 903, the method generates a three-dimensional computer model of the articulatable camera 211 and articulatable surgical tools 231, 241 extending out of the distal end of the entry guide 200 using the information received in 902 and the forward kinematics and known constructions of the instruments 211, 231, 241, entry guide 200, and entry guide manipulator 202. The generated computer model in this example may be referenced to the remote center reference frame (X, Y, Z axes) depicted in FIG. 5. Alternatively, the generated computer model may be referenced to a reference frame defined at the distal end of the entry guide 200. In this latter case, if the orientation and extension of the entry guide 200 from the remote center does not have to be accounted for in the auxiliary view that is being generated by the method, then the position and orientation information for the entry guide 200 may be omitted in 902.

Figure 10:
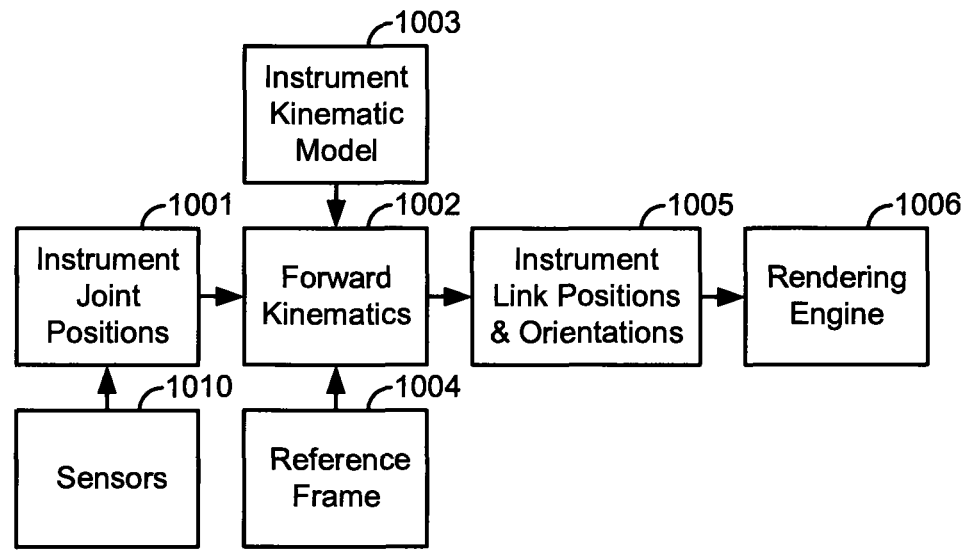
FIG. 10 illustrates a data and processing flow diagram to determine instrument link positions and orientations using instrument joint positions and forward kinematics, as used in a medical robotic system utilizing aspects of the present invention.

For example, referring to FIG. 10, if the state information received in 902 is the instruments' joint positions 1001, such as from sensors 1010, then this information may be applied to the instruments' forward kinematics 1002 using the instruments' kinematic models 1003 to generate the instruments' link positions and orientations 1005 relative to reference frame 1004. The same process may also be generally applied if the state information received in 902 is sensed states of the joggle coupling and gear mechanisms in the manipulator/instrument interfaces.

Figure 11:
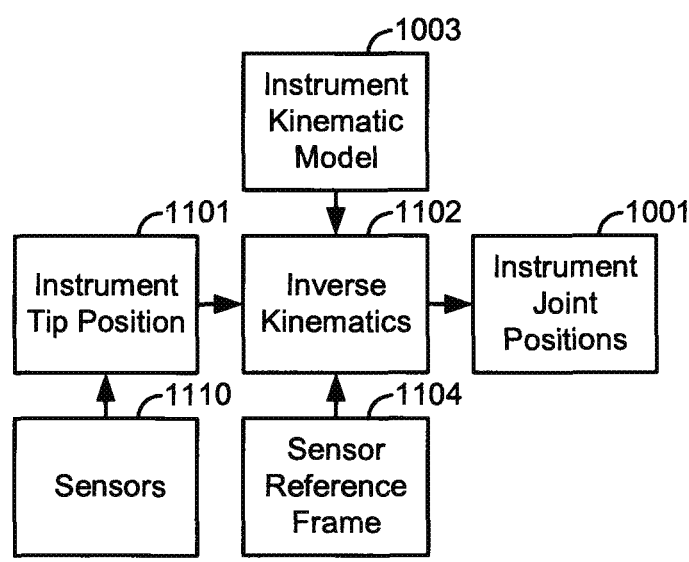
FIG. 11 illustrates a data and processing flow diagram to determine instrument joint positions using a sensed instrument tip position and inverse kinematics, as used in a medical robotic system utilizing aspects of the present invention.

On the other hand, referring to FIG. 11, if the state information received in 902 is the instruments' tip positions 1101 (in the reference frame 1004), such as from sensors 1110, then this information may be applied to the instruments' inverse kinematics 1102 using the instruments' kinematic models 1003 and the sensor reference frame to generate the instruments' joint positions 1001. The instruments' joint positions 1001 may then be applied as described in reference to FIG. 10 to generate the instruments' link positions and orientations 1005 relative to reference frame 1004.

Alternatively, also referring to FIG. 11, if the state information provided in 902 is limited to only the camera's tip position, then the positions of the tips of the surgical tools 231, 241 may be determined relative to the camera reference frame by identifying the tips in the image captured by the camera 211 using conventional image processing techniques and then translating their positions to the reference frame 1004, so that the positions of the camera and tool tips may be applied as described in reference to FIGS. 10, 11 to generate the instruments' link positions and orientations 1005 relative to the reference frame 1004.

Figure 12:
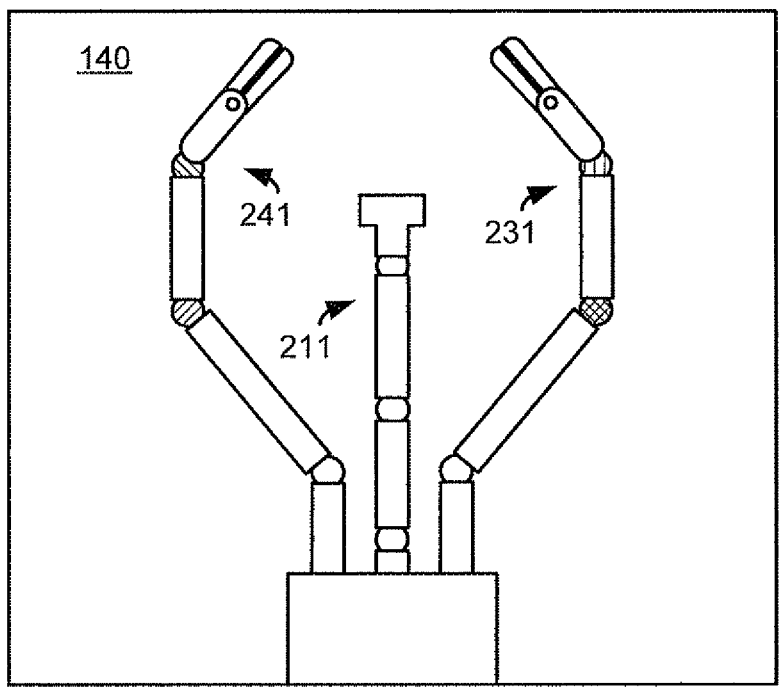
FIGS. 12-13 respectively illustrate top and side auxiliary views as generated and displayed on a display screen by a method implemented in a medical robotic system utilizing aspects of the present invention.
Figure 13:
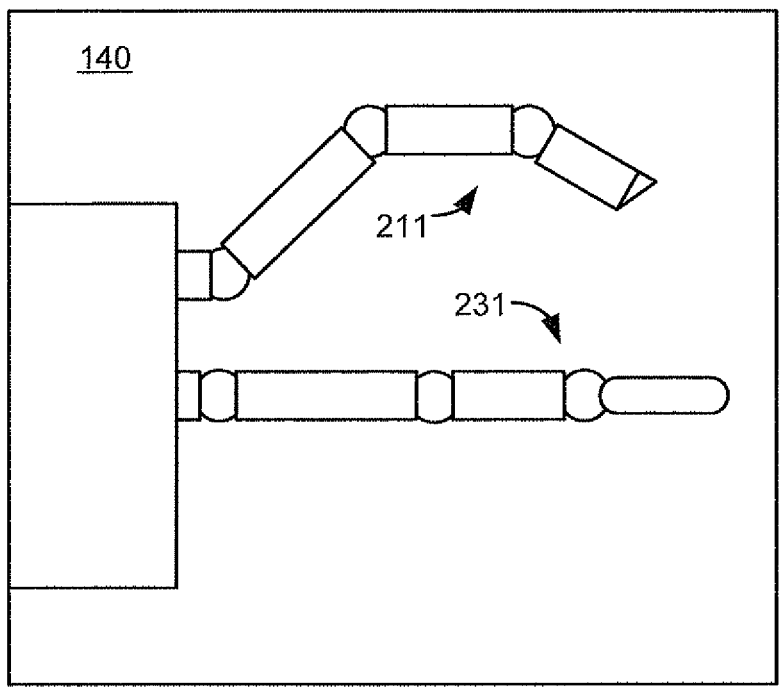

In 904, the method adjusts the view of the computer model of the articulatable camera 211 and articulatable surgical tools 231, 241 extending out of the distal end of the entry guide 200 in the three-dimensional space of the reference frame to a specified viewing point (wherein the term "viewing point" is to be understood herein to include position and orientation). For example, FIG. 12 illustrates a top view of the articulatable camera 211 and articulatable surgical tools 231, 241 extending out of the distal end of the entry guide 200 which corresponds to a viewing point above and slightly behind the distal end of the entry guide 200. As another example, FIG. 13 illustrates a side view of the articulatable camera 211 and articulatable surgical tools 231, 241 extending out of the distal end of the entry guide 200 which corresponds to a viewing point to the right and slightly in front of the distal end of the entry guide 200. Note that although the auxiliary views depicted in FIGS. 12-13 are two-dimensional, they may also be three-dimensional views since three-dimensional information is available from the generated computer model. In this latter case, the auxiliary display screen 140 that they are being displayed on would have to be a three-dimensional display screen like the monitor 104.

Figure 6:
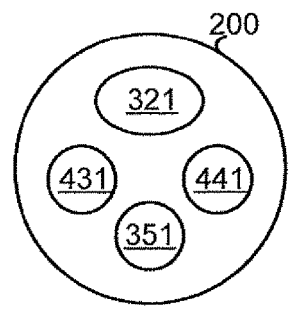
FIG. 6 illustrates a cross-sectional view of an entry guide with passages defined therein that extend between its proximal and distal ends as used in a medical robotic system utilizing aspects of the present invention.

The viewing point may be set at a fixed point such as one providing an isometric (three-dimensional) view from the perspective shown in FIG. 12. This perspective provides a clear view to the surgeon of the articulatable camera 211 and the articulatable surgical tools 231, 241 when the tools 231, 241 are bent "elbows out" as shown (which is a typical configuration for performing a medical procedure using the surgical tools 231, 241). On the other hand, when a third surgical tool is being used (e.g., inserted in the passage 351 shown in FIG. 6), a side view from the perspective of FIG. 13 may additionally be useful since the third surgical tool may be beneath the articulatable camera 211 and therefore obscured by it in the perspective shown in FIG. 12.

Figure 16:
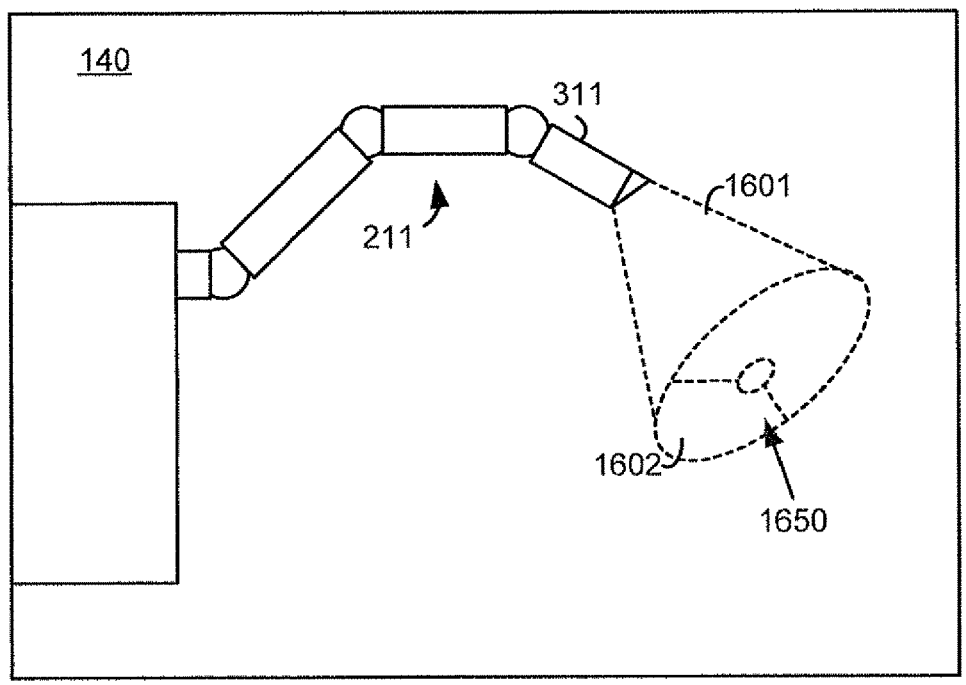
FIG. 16 illustrates an auxiliary side view of an articulatable camera having a frustum as generated and displayed by a method implemented in a medical robotic system utilizing aspects of the present invention on a display screen.
Figure 17:
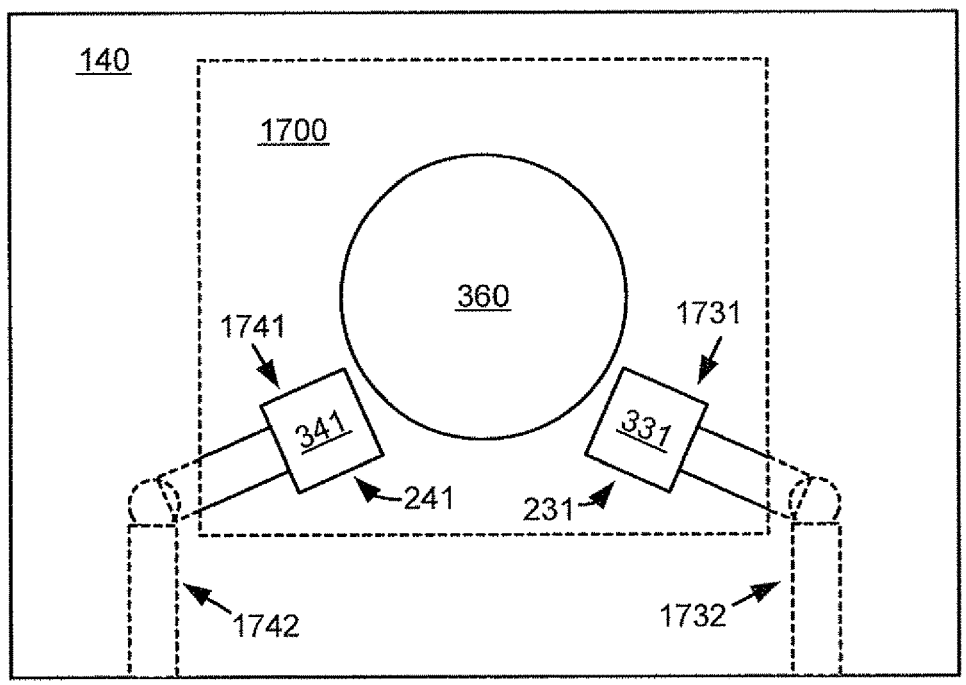
FIG. 17 illustrates a combined display of an auxiliary view of a pair of articulatable surgical tools from a viewing point of a camera, along with an image captured by the camera, as generated and displayed by a method implemented in a medical robotic system utilizing aspects of the present invention on a display screen.
Figure 18:
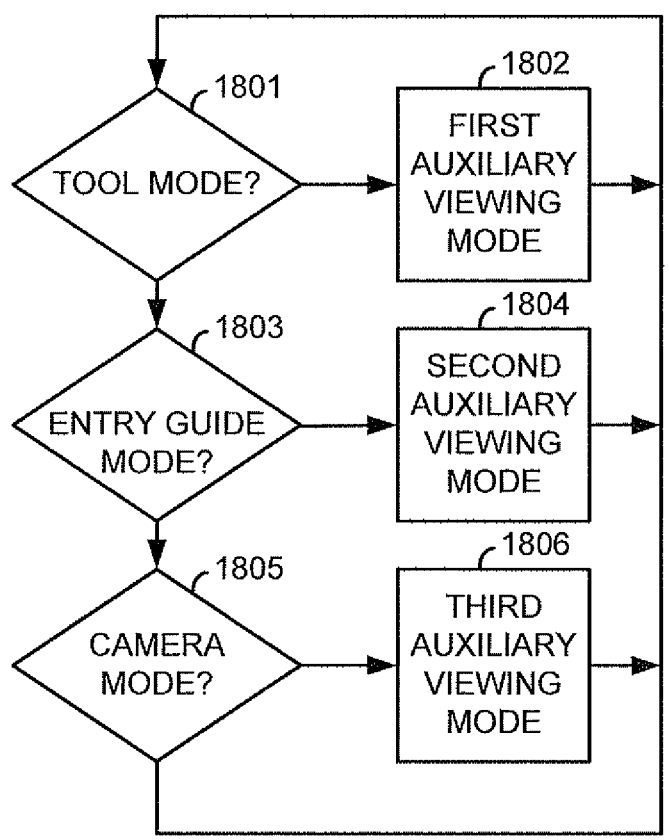
FIG. 18 illustrates a flow diagram of a method for providing auxiliary viewing modes that correspond to device control modes in a medical robotic system, utilizing aspects of the present invention.

Rather than setting the viewing point to a fixed point at all times, the viewing point may also be automatically changed depending upon the control mode (i.e., one of the modes described in reference to FIG. 2) that is operative at the time. As an example, FIG. 18 illustrates a method for automatically changing the auxiliary viewing mode depending upon the control mode currently operative in the medical robotic system 100. In particular, using this method, a first auxiliary viewing mode is performed in 1802 when the medical robotic system 100 is determined in 1801 to be in a tool following mode, a second auxiliary viewing mode is performed in 1804 when the medical robotic system 100 is determined in 1803 to be in an entry guide positioning mode, and a third auxiliary viewing mode is performed in 1806 when the medical robotic system 100 is determined in 1805 to be in a camera positioning mode. The viewing modes for each control mode are selected so as to be most beneficial to the surgeon for performing actions during that mode. For example, in the tool following and camera positioning modes, either or both the surgical tools 231, 241 and camera 211 is being moved at the time and therefore, an auxiliary view of the articulatable camera 211 and articulatable surgical tools 231, 241 extending out of the distal end of the entry guide 200, such as depicted in FIGS. 12 and 13, is useful to avoid collisions between links that are out of the field of view of the camera 211. On the other hand, in the entry guide positioning mode, the articulatable camera 211 and the articulatable surgical tools 231, 241 are locked in position relative to the entry guide 200 and therefore, an auxiliary view providing information on other things such as depicted in FIGS. 16 and 17 may be useful.

Alternatively, operator selectable means for changing the viewing point during the performance of a medical procedure may be provided. For example, the GUI 170 or voice recognition system 160 may be adapted to provide an interactive means for the Surgeon to select the viewing mode and/or change the viewing point of an auxiliary view of the articulatable camera 211 and/or articulatable surgical tools 231, 241 as they extend out of the distal end of the entry guide 200. Buttons on the input devices 108, 109 or the foot pedal 105 may also be used for Surgeon selection of viewing modes. For the Assistant(s), the input device 180 may be used along with a GUI associated with the display screen 140' for selection of viewing modes. Thus, the viewing modes that the Surgeon and Assistant(s) see at the time may be optimized for their particular tasks at the time. Examples of such operator selectable viewing modes and viewing angles are depicted in FIGS. 12-17.

In 905, the method renders the computer model. Rendering in this case includes adding three-dimensional qualities such as known construction features of the instruments 211, 231, 241 and the distal end of the entry guide 200 to the model, filling-in any gaps to make solid models, and providing natural coloring and shading. In addition, rendering may include altering the color or intensity of one or more of the instruments 211, 231, 241 (or one or more of their joints or links or portions thereof) so that the instrument (or joint or link or portion thereof) stands out for identification purposes.

Alternatively, the altering of the color, intensity, or frequency of blinking on and off (e.g., flashing) of one or more of the instruments 211, 231, 241 (or their joints, links, or portions thereof) may serve as a warning that the instrument (or joint or link or portion thereof) is approaching an undesirable event or condition such as nearing a limit of its range of motion or getting too close to or colliding with another one of the instruments. When color is used as a warning, the color may go from a first color (e.g., green) to a second color (e.g., yellow) when a warning threshold of an event to be avoided (e.g., range of motion limitation or collision) is reached, and from the second color to a third color (e.g., red) when the event to be avoided is reached. When intensity is used as a warning, the intensity of the color changes as the instrument (or portion thereof) moves past the warning threshold towards the event to be avoided with a maximum intensity provided when the event is reached. When blinking of the color is used as a warning, the frequency of blinking changes as the instrument (or portion thereof) moves past the warning threshold towards the event to be avoided with a maximum frequency provided when the event is reached. The warning threshold may be based upon a range of motion of the instrument (or portion thereof, such as its joints) or upon a distance between the instrument (or portion thereof) and another instrument (or portion thereof) that it may collide with. Velocity of the instrument's movement may also be a factor in determining the warning threshold. The warning threshold may be programmed by the operator, using the GUI 170, for example, or determined automatically by a programmed algorithm in the processor 102 that takes into account other factors such as the velocity of the instruments' movements.

Alternatively, the altering of the color, intensity, or frequency of blinking on and off (e.g., flashing) of one or more of the instruments 211, 231, 241 (or their joints, links, or portions thereof) may serve as an alert that the instrument (or joint or link or portion thereof) is approaching a desirable event or condition such as an optimal position or configuration for performing or viewing a medical procedure. In this case, an alert threshold may be defined so that the color, intensity, and/or blinking of the one or more of the instruments 211, 231, 241 (or their joints, links, or portions thereof) may change in a similar manner as described previously with respect to warning thresholds and undesirable events or conditions, except that in this case, the change starts when the alert threshold is reached and maximizes or otherwise ends when the desirable event or condition is reached or otherwise achieved. The alert threshold may also be programmed by the operator or determined automatically by a programmed algorithm in a conceptually similar manner as the warning threshold.

Figure 14:
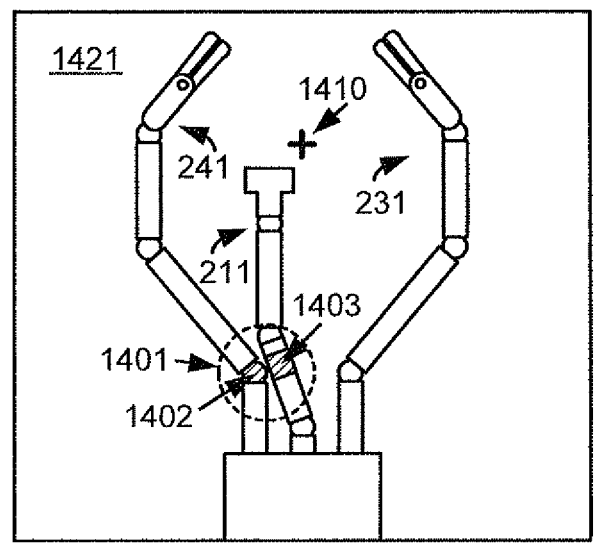
FIG. 14 illustrates top and side auxiliary views as generated and displayed in separate windows on a display screen by a method implemented in a medical robotic system utilizing aspects of the present invention.
Figure 14:
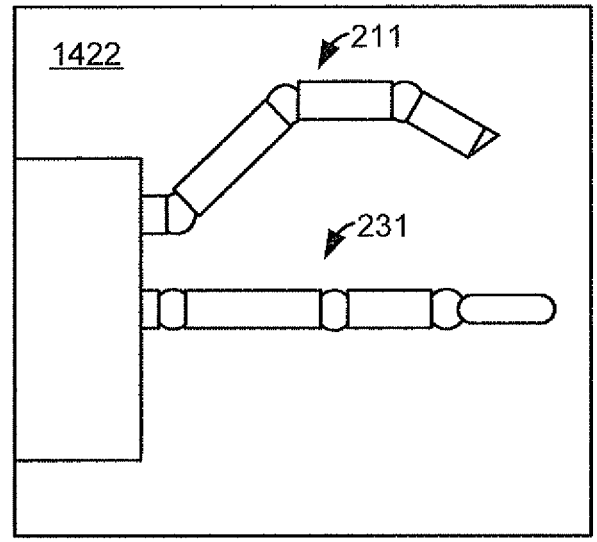
Figure 15:
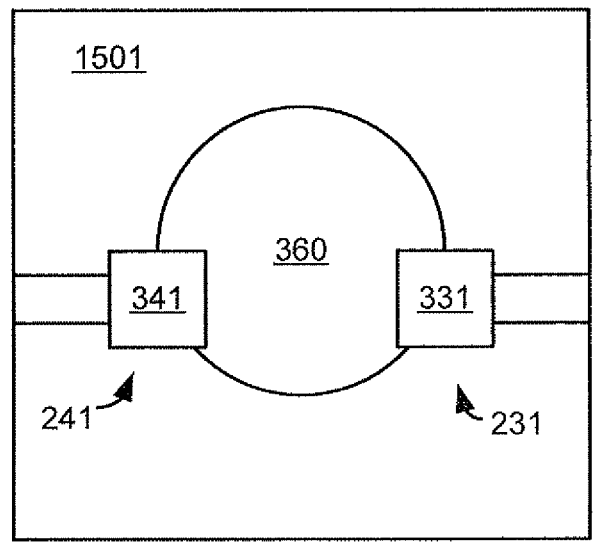
FIG. 15 illustrates an auxiliary view displayed adjacent to an image captured by the articulatable camera on a monitor in a medical robotic system utilizing aspects of the present invention.
Figure 15:
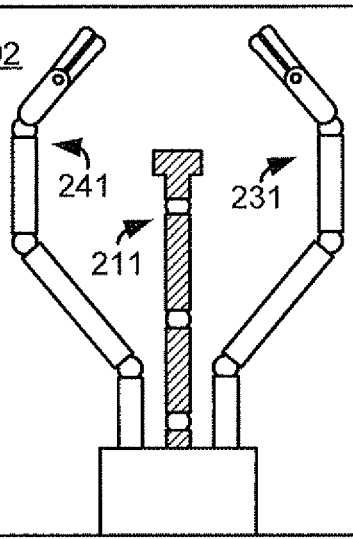

As an example of such highlighting of an instrument for identification, warning or alerting purposes, FIG. 15 shows an auxiliary view of the camera 211 and surgical tools 231, 241 in a window 1502, where the camera 211 has been highlighted. As an example of such highlighting of joints of instruments for identification, warning or alerting purposes, FIG. 12 shows joints of the surgical tools 231, 241 that have been highlighted. As an example of highlighting portions of instruments for warning purposes, FIG. 14 shows a portion 1402 of the surgical tool 241 and a portion 1403 of the camera 211 highlighted to indicate that these portions are dangerously close to colliding.

Rendering may also include overlaying the image captured by the camera 211 over the auxiliary view when the viewing point of the auxiliary image is the same as or directly behind that of the camera 211. As an example, FIG. 17 illustrates a captured image 1700 of the camera 211 rendered as an overlay to an auxiliary view of surgical tools 231, 241 which has been generated from a viewing point of (or right behind) the camera 211. In this example, the auxiliary view of the surgical tools 231, 241 being displayed on the auxiliary display screen 140 (and/or the auxiliary display screen 140') includes portions (e.g., 1731, 1741) in the overlaying captured image 1700 and portions (e.g., 1732, 1742) outside of the overlaying captured image 1700. Thus, the portions of the surgical tools 231, 241 outside of the captured image 1700 provide the Surgeon with additional information about their respective links or articulating arms that are out of the field of view of the camera 211. Highlighting of the instrument portions (e.g., 1732, 1742) outside of the captured image 1700 may also be done for identification purposes or to indicate a warning or alerting condition as described above. Overlaying the captured image 1700 onto the auxiliary view also has the advantage in this case of showing an anatomic structure 360 which is in front of the surgical tools 231, 241 that would not otherwise normally be in the auxiliary view. Although this example shows the captured image 1700 overlaying the auxiliary view on the auxiliary display screen 140, in another rendering scheme, the auxiliary view may overlay the captured image that is being displayed on the monitor 104.

Rather than overlaying the captured image, rendering may also include using the auxiliary view to augment the image captured by the camera 211 by displaying only the portions of the instruments 231, 241 that are not seen in the captured image (i.e., the dotted line portion of the instruments 231, 241 in FIG. 17) in proper alignment and adjacent the captured image in a mosaic fashion.

In addition to, or in lieu of, overlaying the captured image over the auxiliary view or augmenting the captured image with the auxiliary view, rendering may also include providing other useful information in the auxiliary view. As an example, FIG. 16 illustrates an auxiliary side view of an articulatable camera 211 with a frustum 1601 rendered on the auxiliary view so as to be displayed on the auxiliary display 140 as emanating from, and moving with, the camera tip 311. Note that although the frustum 1601 is shown in the figure as a truncated cone, it may also appear as a truncated pyramid to correspond to the captured image that is shown on the monitor 104. The sides of the frustum 1601 indicate a viewing range of the camera 211 and the base 1602 of the frustum 1601 displays an image 1650 that was captured by the camera 211. Note that for simplification purposes, the surgical tools 231, 241 normally in the auxiliary view have been removed for this example. As another example, FIG. 14 shows a semi-translucent sphere or bubble 1401 (preferably colored red) which is displayed by the method as part of the rendering process when a warning threshold is reached so as to indicate to the operator that the highlighted portions 1402, 1403 of the surgical tool 241 and camera 211 are dangerously close to colliding. In this case, the highlighted portions 1402, 1403 are preferably centered within the sphere. As yet another example, FIG. 14 also shows a marker or other indicator 1410 indicating an optimal position for the camera tip 311 for viewing the end effectors of the surgical tools 231, 241 as they are being used to perform a medical procedure. The optimal position may be determined, for example, by finding a location where the tips of the end effectors are equidistant from a center of the captured image. As another example, an auxiliary view is generated by the processor 102 being programmed to: generate a computer model by using state information of a plurality of instruments, e.g., camera 211 and surgical tools 231, 241, that are extending out of the entry guide 200; and adjust a view of the computer model to a perspective of a fixed viewing point which is different than a viewing point for an image presently capturable by the camera 211. The processor 102 further being programmed to: calculate a centroid for the plurality of instruments; and cause the centroid to be displayed on the display 140 (or monitor 104) along with the adjusted view of the computer model so as to provide an indication of whether the entry guide 200 needs to be repositioned.

In 906, the method causes the rendered computer model (i.e., the auxiliary view) to be displayed on one or more displayed screens (e.g., 140 and 140') from the perspective of the selected viewing point. As shown in FIGS. 12-14 and 16-17, the auxiliary view is displayed on the auxiliary display screen 140. As shown in FIG. 14, more than one auxiliary view may be displayed at one time (e.g., top and side perspectives may be provided at the same time respectively in windows 1421 and 1422). As shown in FIG. 15, the auxiliary view may also be displayed on the primary monitor 104 in a window 1502 that is adjacent to an image captured by the articulatable camera 211 which is being shown in another window 1501. Although the windows 1501 and 1502 appear in this example to be the same size, it is to be appreciated that the position and size of the auxiliary view window 1502 may vary and still be within the scope of the present invention. Also, as previously mentioned, the auxiliary view may be overlayed the captured image in the window 1501 instead of in its own separate window 1502. In such case, the overlayed auxiliary view may be switched on and off by the Surgeon so as not to clutter the captured image during the performance of a medical procedure. The switching on and off in this case may be performed by depressing a button on one of the input devices 108, 109 or depressing the foot pedal 105. Alternatively, it may be done by voice activation using the voice recognition system 160 or through Surgeon interaction with the GUI 170 or using any other conventional function switching means.

After completing 906, the method then loops back to 901 to repeat 901-906 for the next processing cycle of the controller 102.

Although the various aspects of the present invention have been described with respect to a preferred embodiment, it will be understood that the invention is entitled to full protection within the full scope of the appended claims.

We claim:

1. A medical system comprising:
an entry guide; a plurality of instruments extending through and out of a distal end of the entry guide, wherein the plurality of instruments includes an image capturing instrument; a plurality of sensors adapted to generate state information by sensing states of the plurality of instruments; a display; and a processor programmed to: use the state information to generate a computer model of the plurality of instruments, adjust a view of the computer model to a perspective of a first fixed viewing point which is different than a viewing point for an image presently capturable by the image capturing instrument, calculate a centroid of the plurality of instruments, and cause the centroid to be displayed on the display along with the adjusted view of the computer model so as to provide an indication of whether the entry guide needs to be repositioned.

2. The medical system according to claim 1, wherein the image capturing device comprises a stereo camera; and wherein the display is a three-dimensional monitor for displaying a three-dimensional image of a surgical site that has been captured by the stereo camera.

\* \* \* \* \*